US011984227B2

(12) United States Patent
Goede et al.

(10) Patent No.: US 11,984,227 B2
(45) Date of Patent: *May 14, 2024

(54) AUTOMATICALLY DETERMINING A MEDICAL RECOMMENDATION FOR A PATIENT BASED ON MULTIPLE MEDICAL IMAGES FROM MULTIPLE DIFFERENT MEDICAL IMAGING MODALITIES

(71) Applicant: XIFIN, INC., San Diego, CA (US)

(72) Inventors: Patricia Anne Goede, Salt Lake City, UT (US); Martin Jonathan Barrack, Poway, CA (US)

(73) Assignee: XIFIN, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,815

(22) Filed: Sep. 20, 2022

(65) Prior Publication Data

US 2023/0011031 A1  Jan. 12, 2023

Related U.S. Application Data

(63) Continuation of application No. 16/941,309, filed on Jul. 28, 2020, now Pat. No. 11,527,329.

(51) Int. Cl.
*G16H 50/20* (2018.01)
*G06F 18/22* (2023.01)
(Continued)

(52) U.S. Cl.
CPC ............ *G16H 50/20* (2018.01); *G06F 18/22* (2023.01); *G06F 18/251* (2023.01); *G06N 20/00* (2019.01);
(Continued)

(58) Field of Classification Search
None
See application file for complete search history.

(56) References Cited

U.S. PATENT DOCUMENTS

| 3,599,161 A | 8/1971 | Stoughton |
| 4,772,206 A | 9/1988 | Kerr et al. |

(Continued)

FOREIGN PATENT DOCUMENTS

WO    2019/104221 A1    5/2019

OTHER PUBLICATIONS

U.S. Appl. No. 16/849,867, filed Apr. 15, 2020, titled "Visual Annotations on Medical Images"; 54 pages.

(Continued)

*Primary Examiner* — Jay M. Patel
(74) *Attorney, Agent, or Firm* — MASCHOFF BRENNAN; Paul G. Johnson

(57) ABSTRACT

Automatically determining a medical recommendation for a patient based on multiple medical images from multiple different medical imaging modalities. In some embodiments, a method may include receiving a first and second medical images of a patient from first and second medical imaging modalities, mapping a first region of interest (ROI) on the first medical image to a second ROI on the second medical image, generating first annotation data related to the first ROI and second annotation data related to the second ROI, generating first medical clinical data related to the first ROI and second medical clinical data related to the second ROI, inputting, into a machine learning classifier, the first and second annotation data and the first and second medical clinical data, and automatically determining, by the machine learning classifier, a medical recommendation for the patient related to a medical condition of the patient.

23 Claims, 10 Drawing Sheets

(51) Int. Cl.
*G06F 18/25* (2023.01)
*G06N 20/00* (2019.01)
*G06T 7/00* (2017.01)
*G06V 10/00* (2022.01)
*G16H 30/40* (2018.01)
*G16H 50/70* (2018.01)
*G16H 70/20* (2018.01)
*G16H 70/60* (2018.01)

(52) U.S. Cl.
CPC ............ *G06T 7/0012* (2013.01); *G06V 10/00* (2022.01); *G16H 30/40* (2018.01); *G16H 50/70* (2018.01); *G06T 2207/10064* (2013.01); *G06T 2207/10081* (2013.01); *G06T 2207/10088* (2013.01); *G16H 70/20* (2018.01); *G16H 70/60* (2018.01)

(56) References Cited

U.S. PATENT DOCUMENTS

| | | |
|---|---|---|
| 4,959,828 A | 9/1990 | Austin |
| 5,101,436 A | 3/1992 | DeAguiar et al. |
| 5,115,501 A | 5/1992 | Kerr |
| 5,146,552 A | 9/1992 | Cassorla et al. |
| 5,253,362 A | 10/1993 | Nolan |
| 5,423,322 A | 6/1995 | Clark et al. |
| 5,428,357 A | 6/1995 | Haab et al. |
| 5,440,338 A | 8/1995 | Roundy et al. |
| 5,531,988 A | 7/1996 | Paul |
| 5,532,844 A | 7/1996 | Kagami et al. |
| 5,581,682 A | 12/1996 | Anderson et al. |
| 5,583,980 A | 12/1996 | Anderson |
| 5,596,700 A | 1/1997 | Darnell et al. |
| 5,608,872 A | 3/1997 | Schwartz et al. |
| 5,621,871 A | 4/1997 | Jaremko et al. |
| 5,724,985 A | 3/1998 | Snell et al. |
| 5,729,620 A | 3/1998 | Wang |
| 5,734,915 A | 3/1998 | Roewer |
| 5,757,368 A | 5/1998 | Gerpheide et al. |
| 5,806,079 A | 9/1998 | Rivette et al. |
| 5,828,774 A | 10/1998 | Wang |
| 5,832,474 A | 11/1998 | Lopresti et al. |
| 5,835,627 A | 11/1998 | Higgins et al. |
| 5,845,301 A | 12/1998 | Rivette et al. |
| 5,875,249 A | 2/1999 | Mintzer et al. |
| 5,877,819 A | 3/1999 | Branson |
| 5,884,246 A | 3/1999 | Boucher et al. |
| 5,920,317 A | 7/1999 | McDonald |
| 5,986,662 A | 11/1999 | Argiro et al. |
| 5,987,345 A | 11/1999 | Engelmann et al. |
| 6,006,242 A | 12/1999 | Poole et al. |
| 6,023,530 A | 2/2000 | Wilson |
| 6,026,363 A | 2/2000 | Shepard |
| 6,026,494 A | 2/2000 | Foster |
| 6,041,335 A | 3/2000 | Merritt et al. |
| 6,054,990 A | 4/2000 | Tran |
| 6,061,717 A | 5/2000 | Carleton et al. |
| 6,124,858 A | 9/2000 | Ge et al. |
| 6,133,925 A | 10/2000 | Jaremko et al. |
| 6,173,068 B1 | 1/2001 | Prokoski |
| 6,175,841 B1 | 1/2001 | Loiacono |
| 6,177,937 B1 | 1/2001 | Stockham et al. |
| 6,269,366 B1 | 7/2001 | Romano et al. |
| 6,279,014 B1 | 8/2001 | Schilit et al. |
| 6,301,586 B1 | 10/2001 | Yang et al. |
| 6,313,836 B1 | 11/2001 | Russell, Jr. et al. |
| 6,342,906 B1 | 1/2002 | Kumar et al. |
| 6,356,922 B1 | 3/2002 | Schilit et al. |
| 6,369,812 B1 | 4/2002 | Iyriboz et al. |
| 6,389,434 B1 | 5/2002 | Rivette et al. |
| 6,429,878 B1 | 8/2002 | Turek et al. |
| 6,477,460 B2 | 11/2002 | Kepler |
| 6,480,186 B1 | 11/2002 | McCabe et al. |
| 6,484,156 B1 | 11/2002 | Gupta et al. |
| 6,509,915 B2 | 1/2003 | Berman et al. |
| 6,518,952 B1 | 2/2003 | Leiper |
| 6,519,603 B1 | 2/2003 | Bays et al. |
| 6,542,165 B1 | 4/2003 | Ohkado |
| 6,546,405 B2 | 4/2003 | Gupta et al. |
| 6,564,263 B1 | 5/2003 | Bergman et al. |
| 6,545,660 B1 | 8/2003 | Shen et al. |
| 6,611,725 B1 | 8/2003 | Harrison et al. |
| 6,684,379 B2 | 1/2004 | Skoll et al. |
| 6,804,394 B1 | 10/2004 | Hsu |
| 6,839,455 B2 | 1/2005 | Kaufman |
| 6,853,741 B1 | 2/2005 | Ruth et al. |
| 6,925,200 B2 | 8/2005 | Wood et al. |
| 6,947,584 B1 | 9/2005 | Avila et al. |
| 6,970,587 B1 | 11/2005 | Rogers |
| 7,136,518 B2 | 11/2006 | Griffin et al. |
| 7,142,217 B2 | 11/2006 | Howard et al. |
| 7,146,031 B1 | 12/2006 | Hartman et al. |
| 7,148,898 B1 | 12/2006 | Howard et al. |
| 7,161,604 B2 | 1/2007 | Higgins et al. |
| 7,225,011 B2 | 5/2007 | Mielekamp |
| 7,260,248 B2 | 8/2007 | Kaufman et al. |
| 7,453,472 B2 | 11/2008 | Goede et al. |
| 9,208,381 B1 | 12/2015 | Shanmugasundaram |
| 10,650,115 B2 | 5/2020 | Goede |
| 2002/0054059 A1 | 5/2002 | Schneiderman |
| 2002/0055955 A1 | 5/2002 | Lloyd-Jones et al. |
| 2002/0067340 A1 | 6/2002 | Van Liere |
| 2002/0070970 A1 | 6/2002 | Wood et al. |
| 2002/0097320 A1 | 7/2002 | Zalis |
| 2003/0052896 A1 | 3/2003 | Higgins et al. |
| 2004/0078215 A1 | 4/2004 | Dahlin et al. |
| 2004/0205482 A1 | 10/2004 | Basu et al. |
| 2005/0049497 A1 | 3/2005 | Krishnan et al. |
| 2006/0020493 A1 | 1/2006 | Cousineau |
| 2007/0118399 A1 | 5/2007 | Avinash et al. |
| 2010/0257189 A1 | 10/2010 | Campbell |
| 2013/0211230 A1 | 8/2013 | Sperling |
| 2014/0108460 A1 | 4/2014 | Casella Dos Santos |
| 2015/0044098 A1 | 2/2015 | Smart et al. |
| 2015/0262372 A1 | 9/2015 | Cardoso et al. |
| 2016/0253456 A1* | 9/2016 | Goede ............... G06F 16/5866 705/3 |
| 2016/0267222 A1 | 9/2016 | Larcom et al. |
| 2017/0351939 A1 | 12/2017 | Madabhushi et al. |
| 2019/0156947 A1* | 5/2019 | Nakamura ............ G16H 50/20 |
| 2019/0294984 A1* | 9/2019 | Guttmann ............ G06V 40/10 |
| 2022/0007946 A1 | 1/2022 | Ziegle et al. |

OTHER PUBLICATIONS

International Search Report and Written Opinion, as issued in connection with International Patent Application No. PCT/US2021/041384, dated Nov. 4, 2021, 13 pgs.

\* cited by examiner

DIAGNSOSIS: BREAST, RIGHT, INVASIVE DUCTAL CARCINOMA, INVASIVE || LYMPH NODE, RIGHT AXILLARY METASTATIC MAMMARY CARCINOMA ER – NEGATIVE, PR – NEGATIVE, HER2 – NEGATIE (1+) PROLIFERATION INDEX: HIGH
TUMOR LOCATION: RIGHT BREAST CENTRAL ULTRASOUND GUIDED CORE BIOPSY HIGH GRADE. HISTOLOGIC GRADE: GRADE HIGH, SBR 9; TUBULES 3/3; NUCLEAR GRADE: 3/3 MITOSES 3/3.

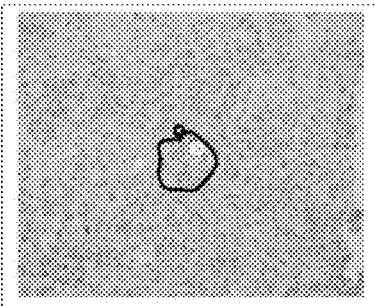
PR- Negative 10X Mag

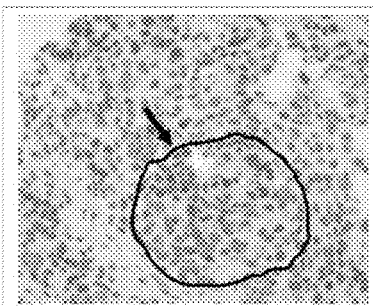
ER-Negative 20X Mag

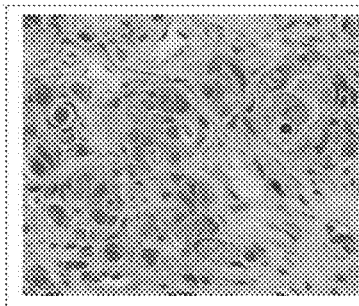
HER2- Negative 40X Mag

FINDINGS: HPI: 59 y/o female who in Nov 2012 was found to have two breast masses in the right breast. One in the 8:00 position and one in the 8-9:00 position. The 9:00 mass was biopsied and showed fibrotic tissue. Right breast- UOQ 3.4 cm palpable mass, possible palpable LN right axilla. Left breast- no palpable masses. Family History: Non-contributory. Patient was told both biopsies were benign so she did not seek treatment.
CLINICAL HISTORY: Prior Reduction Mammoplasty, GERD; Medications: Nexium, Combipatch - discontinued

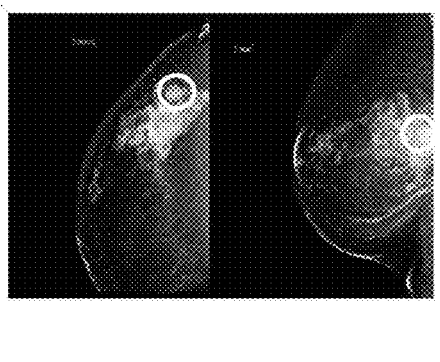
Digital Mammography – mass in Right breast

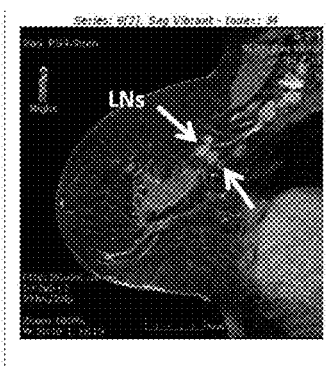
Breast MRI showing affected lymph nodes

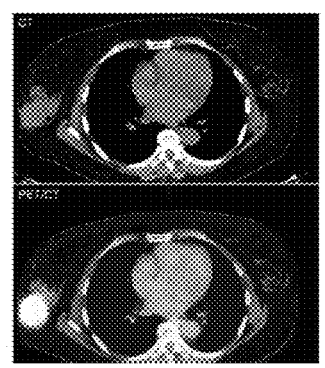
Axial 18F-FDG PET and fused PET/CT uptake

*FIG. 8*

AUTOMATICALLY DETERMINING A MEDICAL RECOMMENDATION FOR A PATIENT BASED ON MULTIPLE MEDICAL IMAGES FROM MULTIPLE DIFFERENT MEDICAL IMAGING MODALITIES

CROSS-REFERENCE TO RELATED APPLICATIONS

This application is a continuation of U.S. patent application Ser. No. 16/941,309, filed on Jul. 28, 2020; the disclosure of which is incorporated herein by reference in its entirety.

BACKGROUND

Medical imaging generally involves creating visual representations of the interior of a patient's body for diagnosis and treatment of a medical condition. Multiple medical images of a single patient may be created using different medical imaging modalities, such as radiology medical images and ultrasound medical images. These different medical images may all be generated in order to diagnose and treat a particular medical condition (e.g., breast cancer).

Unfortunately, conventional imaging systems generally store medical images from different medical imaging modalities in separate systems. Therefore, even where multiple medical images have been generated for a single patient in order to diagnose and treat a particular medical condition (e.g., breast cancer), these medical images are conventionally stored in separate systems, which can make the diagnosis and treatment of the particular medical condition based on the multiple medical images difficult.

The subject matter claimed herein is not limited to embodiments that solve any disadvantages or that operate only in environments such as those described above. Rather, this background is only provided to illustrate one example technology area where some embodiments described herein may be practiced.

SUMMARY

In some embodiments, a computer-implemented method for automatically determining a medical recommendation for a patient based on multiple medical images from multiple different medical imaging modalities may be performed, at least in part, by a computing device including one or more processors. The method may include receiving a first medical image of a patient from a first medical imaging modality and a second medical image of the patient from a second medical imaging modality, with the first medical imaging modality being different from the second medical imaging modality. The method may also include mapping a first region of interest (ROI) on the first medical image to a second ROI on the second medical image, with the first ROI and the second ROI both related to a medical condition of the patient. The method may also include generating first annotation data related to the first ROI and second annotation data related to the second ROI. The method may also include generating first medical clinical data related to the first ROI and second medical clinical data related to the second ROI. The method may also include inputting, into a machine learning classifier, the first and second annotation data and the first and second medical clinical data. The method may also include, in response to the inputting, automatically determining, by the machine learning classifier, a medical recommendation for the patient related to the medical condition of the patient.

In some embodiments, the computer-implemented method may further include training the machine learning classifier with annotation data and medical clinical data of medical images of one or more other patients. In these embodiments, the computer-implemented method may further include receiving a third medical image of the patient from the first medical imaging modality and a fourth medical image of the patient from the second medical imaging modality, mapping a third ROI on the third medical image to a fourth ROI on the fourth medical image with the third ROI and the fourth ROI both related to the medical condition of the patient, generating third annotation data related to the third ROI and fourth annotation data related to the fourth ROI, generating third medical clinical data related to the third ROI and fourth medical clinical data related to the fourth ROI, entering, into the machine learning classifier, the third and fourth annotation data and the third and fourth medical clinical data, and in response to the entering, automatically determining, by the machine learning classifier, an updated medical recommendation for the patient related to the medical condition of the patient. In these embodiments, the entering may further include reinputting, into the machine learning classifier, the first and second annotation data and the first and second medical clinical data.

In some embodiments, the medical recommendation may include one or more of a diagnosis recommendation for the medical condition, a treatment recommendation for the medical condition, and a research recommendation for the medical condition.

In some embodiments, the first medical imaging modality may include a computation tomography (CT) imaging modality, a magnetic resonance imaging (MRI) imaging modality, a histology pathology imaging modality, or a next generation sequenced (NGS) tissue/tumor microarray pathology imaging modality. In these embodiments, the second medical imaging modality may include a tissue microarray (TMA) imaging modality, a Fluorescence In Situ Hybridization (FISH) imaging modality, a flow cytometry pathology imaging modality, a gene or chromosomal microarray pathology imaging modality, or a myocardial perfusion radiology imaging modality.

In some embodiments, the first and second medical clinical data may include measurement data, blood flow data, opaqueness data, abnormality data, cellular structure data, or morphology data.

In some embodiments, one or more non-transitory computer-readable media may include one or more computer readable instructions that, when executed by one or more processors of a computing device, cause the computing device to perform a method for automatically determining a medical recommendation for a patient based on multiple medical images from multiple different medical imaging modalities.

In some embodiments, a computing device may include one or more processors and one or more non-transitory computer-readable media. The one or more non-transitory computer-readable media may include one or more computer-readable instructions that, when executed by the one or more processors, cause the computing device to perform a method for automatically determining a medical recommendation for a patient based on multiple medical images from multiple different medical imaging modalities.

It is to be understood that both the foregoing summary and the following detailed description are explanatory and are not restrictive of the invention as claimed.

BRIEF DESCRIPTION OF THE DRAWINGS

Embodiments will be described and explained with additional specificity and detail through the use of the accompanying drawings in which:

FIG. 8 depicts an example output;

DETAILED DESCRIPTION

Figure 1:
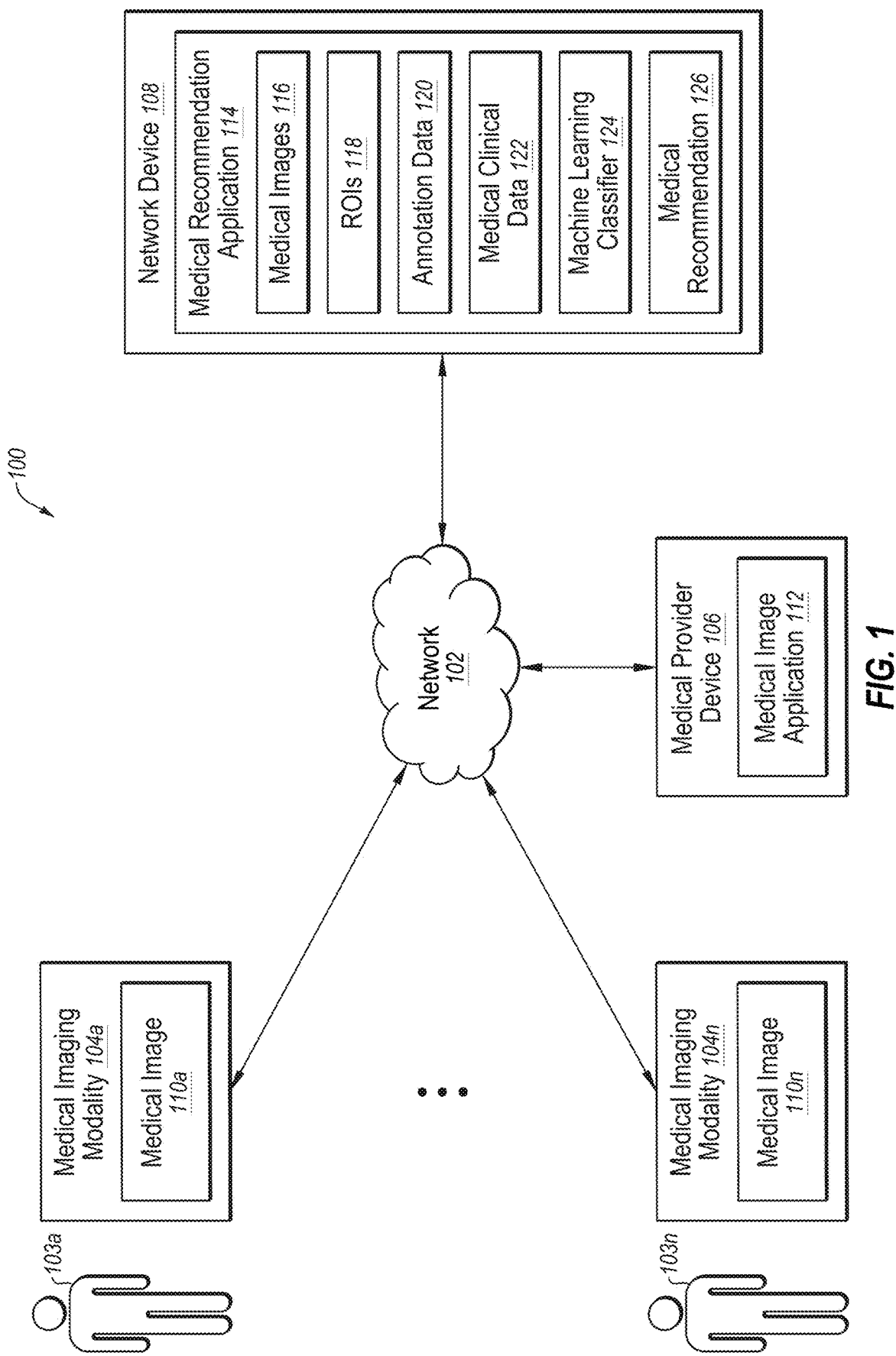
FIG. 1 illustrates an example system configured for automatically determining a medical recommendation for a patient based on multiple medical images from multiple different medical imaging modalities.

Multiple medical images of a single patient may be generated using different medical imaging modalities in order to diagnose and treat a particular medical condition (e.g., breast cancer). Further, each medical image may be further processed by a medical professional annotating a region of interest (ROI) that relates to the particular medical condition in the medical image, and one or more medical professionals (who may be different from the medical professional who performed the annotating of the medical image) may further generate clinical data related to the ROI.

Unfortunately, conventional imaging systems generally store medical images from different medical imaging modalities, as well as medical image annotations and clinical data, in separate systems. Therefore, even where multiple medical images have been generated for a single patient in order to diagnose and treat a particular medical condition (e.g., breast cancer), the storage of these medical images, and their associated annotations and clinical data, in separate systems can make the diagnosis and treatment of the particular medical condition based on the multiple medical images difficult, due at least in part to no mapping of information between the different medical images.

Some embodiments disclosed herein may enable automatically determining a medical recommendation for a patient based on multiple medical images from multiple different medical imaging modalities. For example, a medical recommendation application may receive first and second medical images of a patient (e.g., an MM image and a tissue microarray (TMA) image). The medical recommendation application may then map a first region of interest (ROI) on the first medical image to a second ROI on the second medical image, with the first ROI and the second ROI both related to a medical condition of the patient (e.g., with both ROIs related to breast cancer of the patient). The medical recommendation application may then generate first annotation data related to the first ROI and second annotation data related to the second ROI. The medical recommendation application may then generate first medical clinical data related to the first ROI and second medical clinical data related to the second ROI. The medical recommendation application may input, into a machine learning classifier, the first and second annotation data and the first and second medical clinical data. The medical recommendation application may then automatically determine, using the machine learning classifier, a medical recommendation (e.g., a diagnosis recommendation, a treatment recommendation, or a research recommendation) for the patient related to the medical condition of the patient.

In this manner, some embodiments disclosed herein may aggregate different medical images of a patient that were originally generated using different imaging modalities, as well as associated annotation data and clinical data related to a medical condition of the patient, and may automatically generate a medical recommendation for the patient related to the medical condition using a machine learning classifier.

Further, some embodiments disclosed herein may employ structured annotations and medical data (e.g., treatments, changing diagnoses over time, etc.) and may perform measurements on medical images (e.g., size and shape of tumor, etc.), and may include genetic data and other relevant information and calculations (e.g., opaqueness, blood vessels, other visually measurable characteristics), and compile them in a database upon which calculations may be performed to derive standard determinations that can be applied to new images to assist in diagnoses, treatment, and research. Some embodiments may further continue to learn as new factors are added, and when a statistically significant relationship is identified, some embodiments can propose to add them to its normative guide and, after approval, add that new factor so that the system constantly refines its ability to determine the most likely diagnoses and treatments and likely outcomes.

Turning to the figures, FIG. 1 illustrates an example system 100 configured for automatically determining a medical recommendation for a patient based on multiple medical images from multiple different medical imaging modalities. The system 100 may include a network 102, medical imaging modalities 104a-104n, a medical provider device 106, and a network device 108.

In some embodiments, the network 102 may be configured to communicatively couple the medical imaging modalities 104a-104n, the medical provider device 106, and the network device 108 to one another and to other network devices using one or more network protocols, such as the network protocols available in connection with the World Wide Web. In some embodiments, the network 102 may be any wired or wireless network, or combination of multiple networks, configured to send and receive communications (e.g., via data packets) between systems and devices. In some embodiments, the network 102 may include a Personal Area Network (PAN), a Local Area Network (LAN), a Metropolitan Area Network (MAN), a Wide Area Network (WAN), a Storage Area Network (SAN), a cellular network, the Internet, or some combination thereof.

Figure 10:
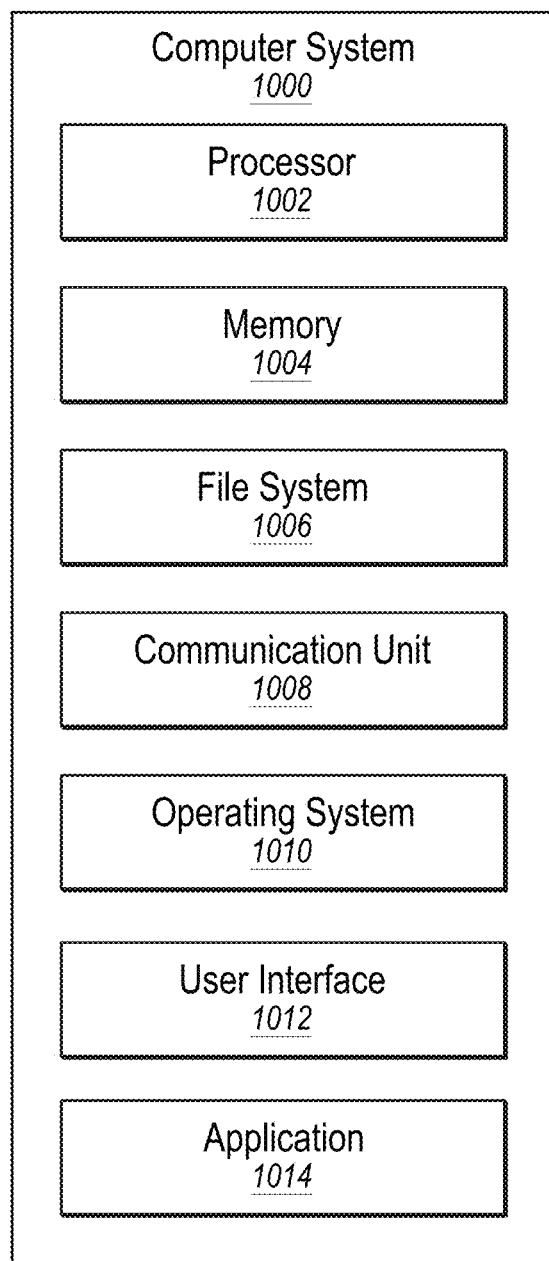
FIG. 10 illustrates an example computer system that may be employed in automatically determining a medical recommendation for a patient based on multiple medical images from multiple different medical imaging modalities.

In some embodiments, the medical imaging modalities 104a-104n may be any computer systems, or combination of multiple computer systems, capable of communicating over the network 102 and capable of generating medical images, such as the medical images 110a-110n, examples of which are disclosed herein in connection with the computer system 1000 of FIG. 10. For example, the medical imaging modalities 104*a*-104*n* may be employed to generate the medical images 110*a*-110*n* of the patients 103*a*-103*n*, or of a single one of the patients (e.g., the patient 103*a*). In some embodiments, the medical imaging modality 104*a* may be different from the medical imaging modality 104*n*. For example, the medical imaging modality 104*a* may include one or more of a computation tomography (CT) imaging modality, a magnetic resonance imaging (MRI) imaging modality, a histology pathology imaging modality, or a next generation sequenced (NGS) tissue/tumor microarray pathology imaging modality, and the medical imaging modality 104*n* may include one or more of a tissue microarray (TMA) imaging modality, a Fluorescence In Situ Hybridization (FISH) imaging modality, a flow cytometry pathology imaging modality, a gene or chromosomal microarray pathology imaging modality, or a myocardial perfusion radiology imaging modality. Other medical imaging modalities may include, or be related to, clinical imaging modalities (e.g., primary care or dermatology, most often derived from a scope, camera or other clinical imaging device) which may be employed in connection with the imaging of wounds, bruising, skin conditions such a moles, nevi and other abnormalities documented by a clinical photograph (image), etc., with common clinical imaging formats including TIF, JPG, PNG, BMP, and GIF. Other medical imaging modalities may include, or be related to, radiology imaging modalities (e.g., Magnetic Resonance Imaging (MM), Computed Tomography (CT), Positron Emission Tomography (PET), Positron Emission Tomography-Computed Tomography (PET/CT), Radiography (x-ray), Ultrasound (US), Mammography, Fluoroscopy, Angiography, etc., with common radiology imaging formats including Digital Imaging and Communications in Medicine (DICOM). Radiology imaging modalities may be used and interpreted by radiologists to see structures inside the body that help to diagnose a health condition. Other medical imaging modalities may include, or be related to, pathology imaging modalities (e.g., Fluorescence In Situ Hybridization (FISH) Flow Cytometry scatter plots, histology including whole slide imaging (WSI), cytogenetics, Polymerase Chain Reaction (PCR) and quantitative multiplexing (qPCR), etc., with common pathology image formats including TIF, JPG, PNG, and plots. FISH can be used to test for the presence or absence of specific chromosome regions and may be used to detect small chromosome deletions. Histology may involve the microanatomy of cells, tissues, and organs as seen through a microscope. Tissue samples may be examined to establish a correlation between structure and function and specifically used in diagnostic processes. Other medical imaging modalities may include, or be related to, genomic, proteomic, or transcriptomic imaging modalities including Next Generation Sequencing (NGS) imaging, etc. Genomics may focus on the structure, function, evolution, mapping, and editing of genomes. A genome generally includes an organism's complete set of DNA, including all of its genes. Proteomic is the study of the proteins in all organisms. Images may be in the form of tumor and/or tissue microarrays (TMA) that contain details about DNA profiles and mutations that are used to perform genetic mapping to help develop understandings around different diseases and used in diagnosis, treatment, and research related to cancer.

In some embodiments, the medical provider device 106 may be any computer system, or combination of multiple computer systems, capable of communicating over the network 102 and capable of running a medical image application 112, examples of which are disclosed herein in connection with the computer system 1000 of FIG. 10. In some embodiments, the medical image application 112 may be employed by a medical provider (e.g., a medical doctor, a radiologist, etc.) to annotate medical images and/or to associate clinical data with medical images. In some embodiments, medical clinical data may include measurement data, blood flow data, opaqueness data, abnormality data, cellular structure data, or morphology data. Other medical clinical data may include, or be related to, clinical history, past medical history, social history, radiology initial findings from radiology imaging, a diagnostic pathology report, clinical notes from multi-disciplinary teams discussions (e.g., a tumor board), NGS reports (mutations and variants of unknown significance), treatment plan(s), drug regimens and formularies, drug interactions, best supportive care, cancer stage, histologic tumor grade, physiology, heterogeneity, spatial measurements from anatomy, magnification (both radiology and pathology), and any metadata that is part of an imaging study including, but not limited to, radiology, contrast, stain, stain aliquot, magnification, and annotations.

In some embodiments, the network device 108 may each be any computer system, or combination of multiple computer systems, capable of communicating over the network 102 and capable of hosting a medical recommendation application 114, examples of which are disclosed herein in connection with the computer system 1000 of FIG. 10. In some embodiments, the medical recommendation application 114 may automatically receive the medical images 116 from the medical imaging modalities 104*a*-104*n*. The medical recommendation application 114 may also automatically receive (e.g., from the medical image application 112) and/or generate one or more ROIs 118 on the medical images 116, which the medical recommendation application 114 may map between the medical images 116, such as where two ROIs on two separate medical images relate to a single medical condition (e.g., breast cancer) of a single patient (e.g., the patient 103*a*). The medical recommendation application 114 may also receive (e.g., from the medical image application 112) and/or generate annotation data 120 related to the ROIs 118. The medical recommendation application 114 may also receive (e.g., from the medical image application 112) and/or generate medical clinical data 122 related to the ROIs 118. The medical recommendation application 114 may then input, into a machine learning classifier 124, the annotation data 120 and the medical clinical data 122 to allow the machine learning classifier to automatically generate a medical recommendation 126 (e.g., a diagnosis recommendation, a treatment recommendation, or a research recommendation) for the patient 103*a* related to the medical condition (e.g., breast cancer) of the patient 103*a*. In this manner, medical recommendation application 114 may aggregate different medical images 116 of the patient 103*a* that were originally generated using the different medical imaging modalities 104*a* and 104*n*, as well as associated annotation data 120 and medical clinical data 122 related to a medical condition of the patient 103*a*, and may automatically generate a medical recommendation 126 for the patient 103*a* related to the medical condition using the machine learning classifier 124.

In some embodiments, prior to or between uses by the medical recommendation application 114, the machine learning classifier 124 may be trained/retrained with annotation data and medical clinical data of medical images of multiple patients. Further, the machine learning classifier 124 may be used to automatically generate, or repeatedly update, the medical recommendation 126 for a patient (e.g., the patient 103a) related to a medical condition of the patient using more than two medical images. Further, the machine learning classifier 124 may employ rule sets that allow for machine learning algorithms to derive information from data sets.

Modifications, additions, or omissions may be made to the system 100 without departing from the scope of the present disclosure. For example, in some embodiments, the system 100 may include additional components similar to the components illustrated in FIG. 1 that each may be configured similarly to the components illustrated in FIG. 1.

Figure 2:
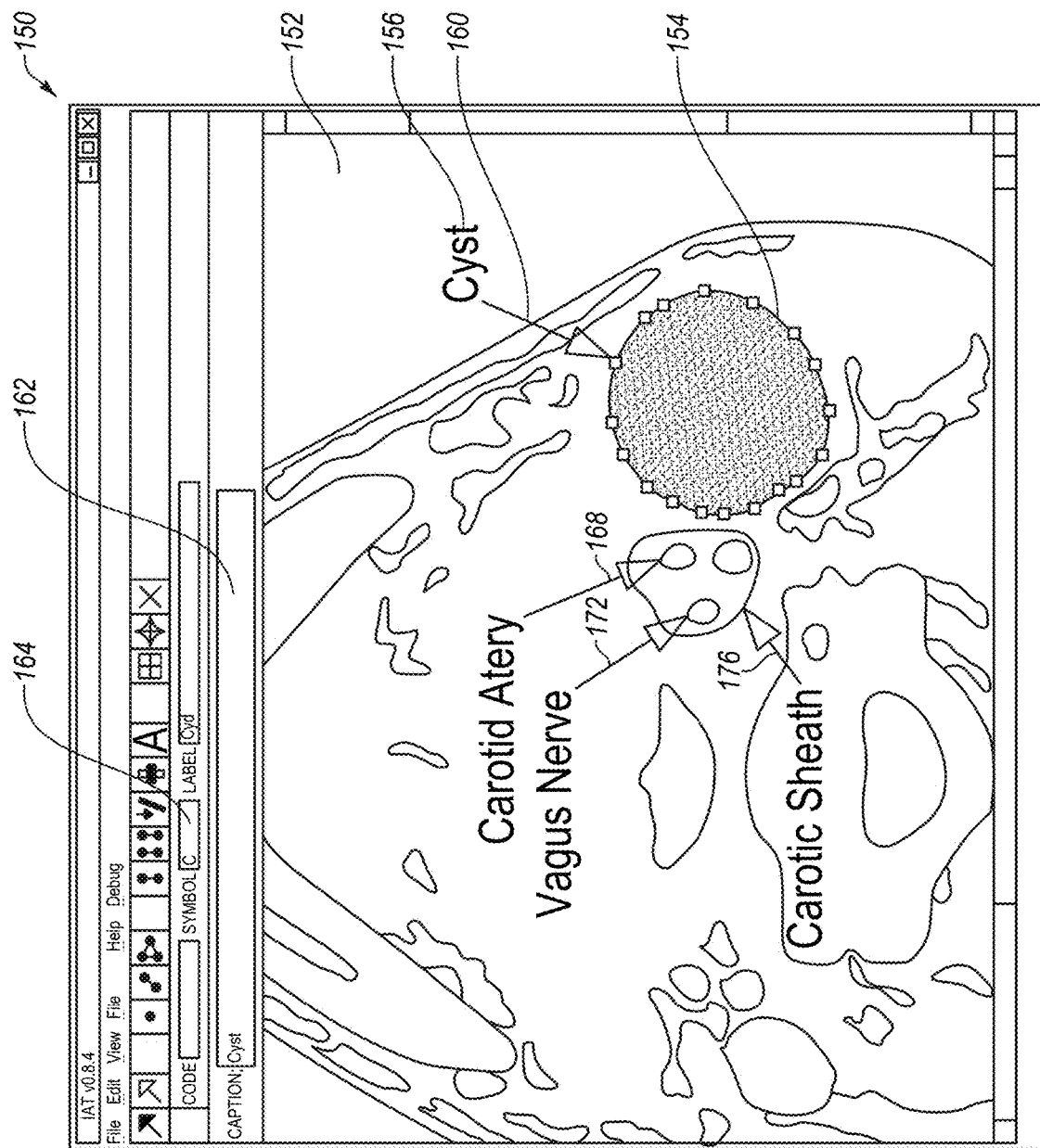
FIG. 2 is a depiction of a display showing various features of an embodiment.

FIG. 2 is a depiction of a display showing various features of an embodiment. As disclosed in FIG. 2, a display 150 may include an image 152 and annotations. More specifically, display 150 includes several regions of interest (ROIs) associated with image 152. In some embodiments, an ROI may include, but is not limited to, a feature contained in a medical image (e.g., nodule(s), cells, morphology, gross anatomy, structure, color, shape, name, etc.). An ROI in radiology may be different than a region of interest in pathology (e.g., radiology is clinical and represents gross anatomy where pathology is microscopic or cellular and represents diagnostic). Genetic/genomic data may also contain annotated ROIs at the DNA or molecular level that can be mapped to the images from radiology and pathology imaging modalities (e.g., tumor/tissue microarray).

One region of interest, as indicated by reference numeral 154, is noted by a label 156 (i.e., "Cyst"), which is connected to region of interest 154 by a pointer 160. In addition, display 150 includes a caption 162 and a symbol 164 for region of interest 154. Display 150 also includes label (i.e., "Carotid Artery") connected to the depicted carotid artery via pointer 168, a label (i.e., "Vagus Nerve") connected to the depicted vagus nerve via a pointer 172, and a label (i.e., "Carotic Sheath") connected to the depicted carotic sheath via a pointer 176. As will be appreciated, the annotations are useful in conveying information to an observer.

In accordance with an embodiment of the present disclosure, a separate annotation file may contain an identifier that corresponds to the image file in case the two files are separated. Further, each image file may include properties and metadata (e.g., subject-predicate-object) that contain the properties of the image, metadata about the image, annotations for the image, relationships with other images from the same or different modalities, etc.). As will be explained in greater detail below, reuse of the image is facilitated since the original image remains unchanged and the annotations remain linked to the image. It will be appreciated that because the annotations are not embedded into the image, they can be referenced, grouped (as shown in FIG. 2) and indexed for a variety of purposes. In addition, while multiple annotations can be added to an image, not all of the annotations need be displayed at the option of the presenter, to create a context appropriate annotated image. These multiple annotations can be interactive.

Figure 3A:
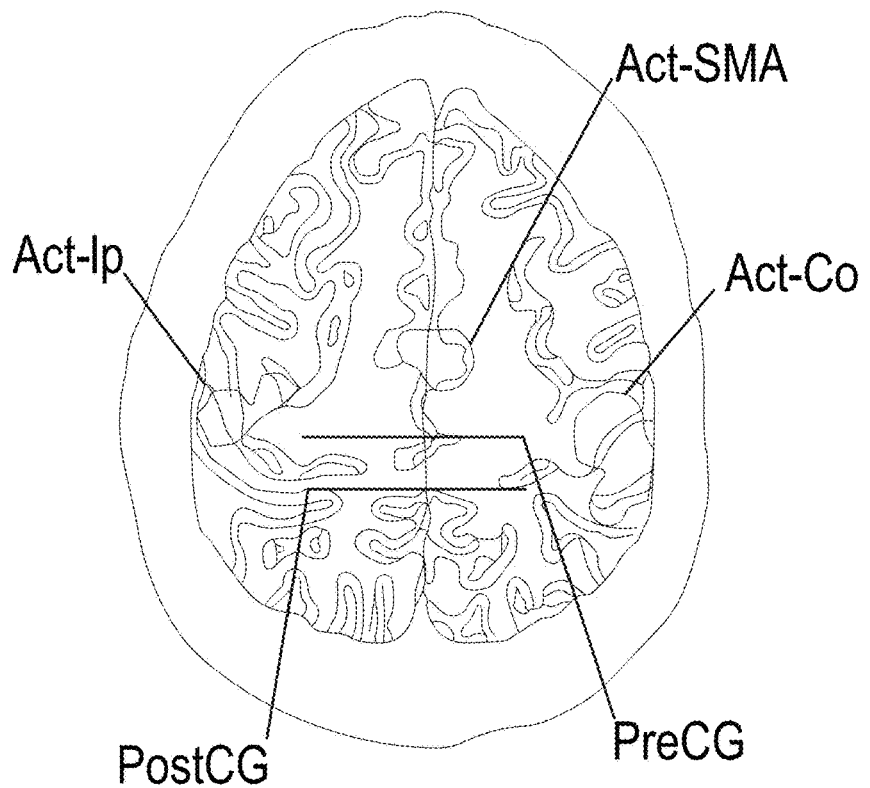
FIG. 3A illustrates an image and annotations.
Figure 3B:
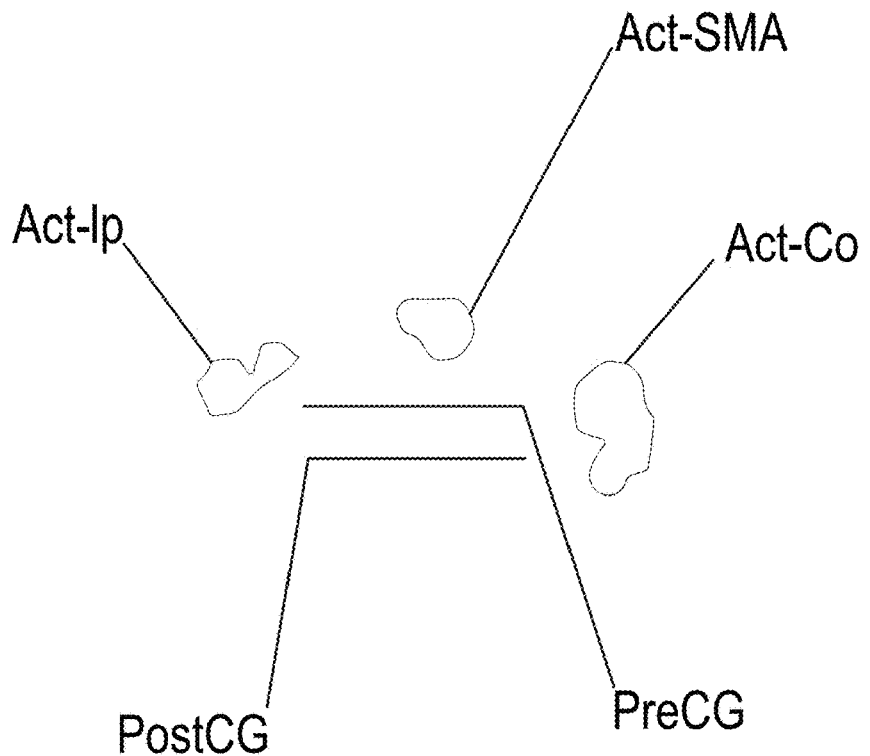
FIG. 3B illustrates non-embedded nature of the annotations in FIG. 3A.

FIG. 3A illustrates an image and annotations, and FIG. 3B illustrates non-embedded nature of the annotations in FIG. 3A. More particularly, FIGS. 3A and 3B respectively depict a display including an image and a display including the annotations without the image. FIG. 3A illustrates marked regions of interest with respective pointers and labels. As will be appreciated, the annotations may be "overlaid" over the original image and not embedded. Rather, the annotations may be stored in a separate file, which may be linked to the image file. In one specific example, the annotations may be stored in an image independent vector format (i.e., for high-resolution display at all scales). It is noted that the image is unedited and no pixels of the original raster image were modified.

Figure 4:
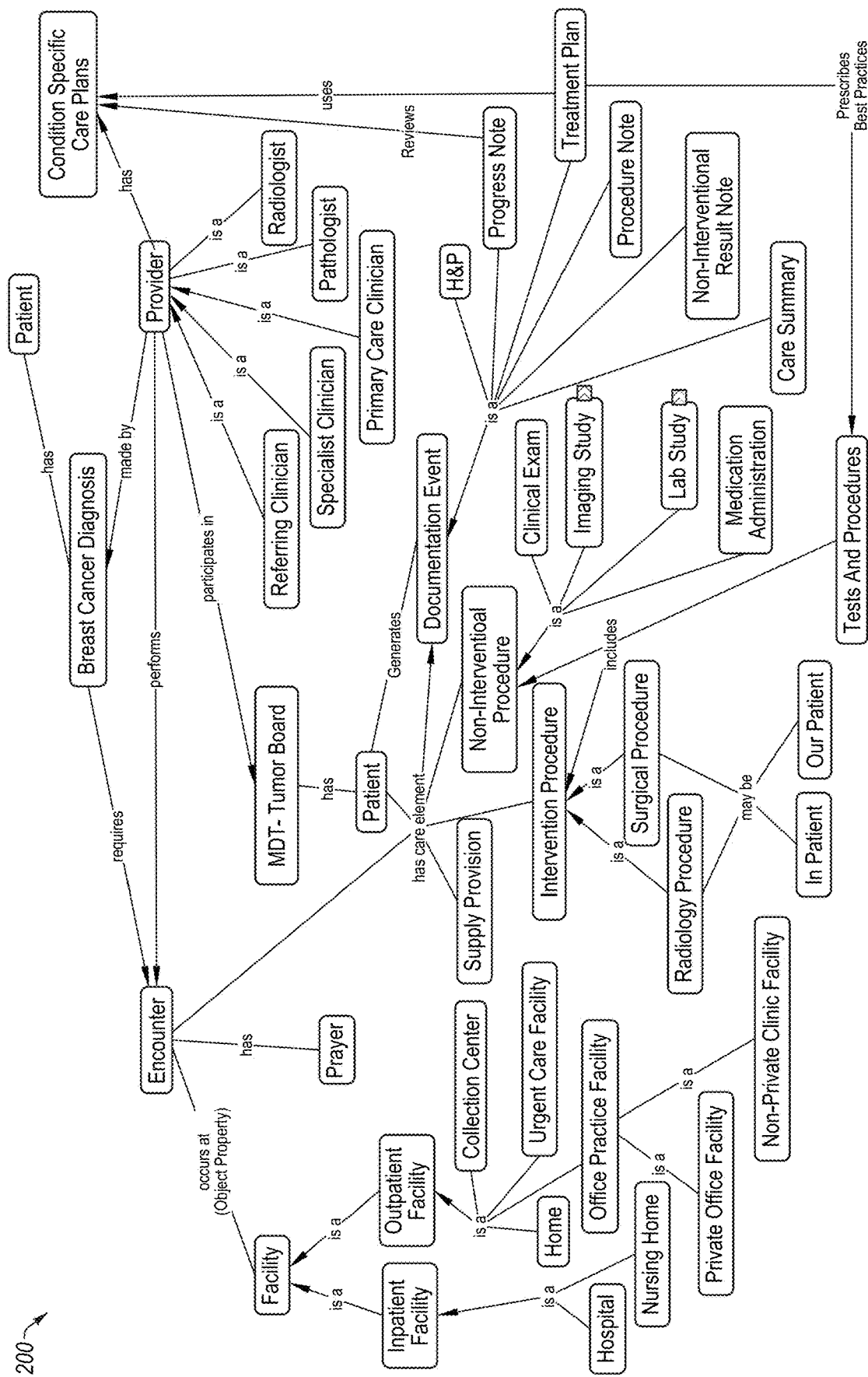
FIG. 4 depicts a map illustrating various stages of a treatment process.

FIG. 4 depicts a map illustrating various stages of a treatment process. More particularly, FIG. 4 depicts a cognitive map 200, which illustrates the complex nature and stages of a medical treatment process. As will be understood by a person having ordinary skill in the art, a treatment process may involve various stages and interaction amongst various healthcare personnel from multiple healthcare specialties. Further, the treatment process may include interaction with images, patient information, payers, and a patient.

As will be appreciated, diagnostics and treatment planning may be dependent on bringing members of a care team together for routine review and updates of a treatment plan. For example, in a breast cancer case (e.g., see FIG. 4), data (e.g., imaging and textual inputs) from different specialties (e.g., radiology, surgery, pathology, etc.) perform a critical role in diagnosis. The data may originate from different encounters generated at different times during treatment of a patient. Treatment requires ongoing collaboration between health care professionals (e.g. expert clinicians) of different specialties that form a multi-disciplinary team, which requires access to the patient's data for critical decision making. Ideally, each healthcare professional should review all the patient's data (e.g., within a tumor board or case review) including image data and annotated areas of concern for a particular patient. Further, text records that provide context for the image review such as radiology, surgical and previous pathology reports, remain vital.

A radiology-pathology-oncology breast cancer example is a common scenario. In this example, a female may receive a mammogram that shows a suspicious mass. The mass may be biopsied and sent to pathology where an initial diagnosis begins with screening and identifying suspicious findings from imaging (e.g., via radiology). Further, tissue diagnosis (e.g., via pathology) imaging may occur. Other types of pathology imaging and oncology imaging are routinely accessed and reviewed in multi-disciplinary team evaluation. Moreover, it is becoming more common that additional studies, using biomarkers and sophisticated molecular imaging, may provide the framework for pathologists to contribute significantly to refine treatment pathways that will become routine in personalized therapy. In the breast cancer example (e.g., wherein a patient is diagnosed with breast cancer), images and data critical to the treatment plan may be generated over an extended time period (e.g., 12-18 months).

Record systems, such as, for example only, electronic medical/health record (EMR/EHR) systems, may be designed to manage and depict information. For example, EMR/EHR systems may be configured to manage and depict administrative, logistical and systematic health information for a patient. Current EMR/EHR systems maintain a rigid view of a patient care process and struggle to integrate disparate information sources and heterogeneous provider systems. EMR systems typically do not meet the requirements of a fully engaged multi-disciplinary team process, especially when members of a care team are from disparate organizations. Further, conventional EMR systems may fail to integrate multi-modal imagery, complete annotation, and incorporate multi-disciplinary team contributions to diagnosis, treatment planning, and treatment plan execution.

Further, in the medical field, for example, text-based patient information (e.g., findings, diagnoses and clinical summaries) may reside in separate information systems, which may prohibit timely access by a care team. For example, clinical notes may reside in an EMR/EHR and in a laboratory information system (LIS), which may not be connected to each other or to the applicable imaging systems.

In addition, some conventional systems, which may manage patient records in a chronological or linear manner, are focused on patient records and are not designed to facilitate or support any level of interactivity (e.g., collaboration including specialized tools for visual annotation and real-time communication). These systems may consume images, provided each image is a manageable size, but without the contextual components about the image or set of images, thus decreasing the ability of the image in the system to help with diagnosis, treatment or research considerations.

Various embodiments of the present disclosure relate to a system configured to support diagnosis, treatment, and/or research of a medical condition of a patient based on multiple medical images from multiple different medical imaging modalities. The system may be configured for exchange and management of data including, for example, images and text. It is noted that data (e.g., images and/or text) having a common identifier may be included within a data set. Stated another way, all data within a data set may have a common identifier, such as a patient ID. In some embodiments, the system may be used by a variety of medical professionals including, but not limited to, radiologists, pathologists, oncologists, gastroenterologists, and primary care physicians.

Compared to conventional systems, which may receive images from a single modality (e.g., radiology), various systems, as described herein, are configured to receive, process, and aggregate data (e.g., text and/or images) from different modalities (e.g., radiology, pathology, oncology, dermatology, GI, etc.) into a data set. Thus, a data set may include data from different image modalities and/or medical specialties to support and facilitate evaluation (e.g., multi-disciplinary team evaluation), review, and treatment planning (e.g., collaboration). According to various embodiments, relationships among data within a data set may be maintained. For example, data within a data set may be linked via metadata.

A system may be configured to provide a presentation layer (e.g., via a computer screen) or portal that allows for real-time communication with data (e.g., images), supporting the iterative nature of a multi-disciplinary team by allowing specialists to access and review critical information, including clinical summaries from other specialists. Bringing specialists and providers together to evaluate imaging and diagnostic summaries for a case, in stages, in a timely manner, may improve the treatment outcome of the patient. For example, a pathologist may consult with a surgeon and an oncologist. At every step in a treatment process, images may be generated from multiple devices that are unlinked to the patient's health record.

Diagnosis and findings may be important for devising a treatment plan and may require interaction across various specialties (e.g., gastroenterology, radiology, surgery, pathology, oncology, pulmonology, primary care, etc.) to identify the correct treatment planning options. Once treatment is underway, studies may be conducted over a time period (e.g., several months) to determine the effectiveness of treatment and to determine whether changes are necessary. Studies (e.g., imaging studies) may be required to measure the effectiveness of treatment and generate data (e.g., textual findings and images). This data may be reviewed by a care team (e.g., radiology, pathology, and oncology) in formal reviews (e.g., case reviews or tumor boards) or informally. Further, additional data (e.g., comments and findings) may be collected regarding the status of, and changes to, the diagnosis and treatment.

In one specific embodiment, a system may process and aggregate images including annotations (e.g., annotated regions of interest) across image specialties and modalities (e.g., radiology, pathology, surgery and oncology), wherein the annotations (e.g., metadata) may maintain relationships across one or more images within a data set. Annotated regions of interest (ROI) may maintain a relationship with an original image that may be part of a data set for a given record or case. Annotated ROI may include annotated information to describe a relationship between and across images from a different modality or modality as a group to convey meaning in diagnosis or treatment. The information may be modified (e.g., across clinical imaging modalities) to reflect a change in a record for a given diagnosis and/or treatment plan.

A system may further be configured to group one or more annotations into discrete elements, wherein the one or more annotations may be displayed with one or more images to maintain the data-derived parent-child relationships across different images and textual data from different data modalities. The one or more annotations may provide context to one or more images and/or text in human-readable and machine-consumable formats. As will be appreciated, in various industries (e.g., healthcare, geography, oil and gas, and satellite industries), annotations, and the ability to produce a context specific collection of annotation groups and their metadata layers may be useful for conveying meaningful information for all aspects of digital imaging. It is noted that although various embodiments of the present disclosure are described with reference to healthcare, the present disclosure is not so limited. Rather, other applications, including, for example, geography applications, oil and gas applications, and satellite applications, are contemplated within the scope of the present disclosure. Further, embodiments of the present disclosure are not limited to digital data.

In another specific embodiment, a system may be configured to aggregate, organize and display field of view (FOV) images, wherein the FOV images can be modified to reflect a change in treatment plan or diagnosis. Further, in one embodiment, annotated regions of interest or one or more FOV images may be included in a standardized format (e.g., the Continuity of Care (CCD) reporting format), which may be compliant with the Clinical Document Architecture (CDA) standard. More specifically, in another embodiment, a system may be configured to aggregate and organize specific images (e.g., FOV images) and their annotated regions of interest for inclusion into structured output (e.g., the CCD structured output (i.e., a standard format)) while maintaining relationships with the data (e.g., images and associated textual data) with external systems via metadata layers of the annotations. Further, a system may generate (e.g., output) a combination of annotation regions of interest captured in a FOV from a combination of encounters (e.g., for the purpose of conveying specific information regarding a diagnosis or change in diagnosis).

In one example, a treating oncologist may be able to review with the multi-disciplinary care team, and with the patient, the annotated regions of interest within different images associated with the diagnosis and generate a CCD integrated output, which can be used for human or system communication such as an electronic medical record (EMR) or electronic health record (EHR).

In one embodiment, the format and type of an output of a system may be a combination of annotation regions of interest captured in a FOV from a combination of encounters (e.g., for the purpose of conveying specific data regarding a diagnosis and/or documentation of relevant changes to a diagnosis). Annotated regions of interest contained in the FOV images may contain relevant data, such as billing codes, lexicons, and vocabularies for external system reference and consumption. The system may index and catalogue all received data for the purpose of search and retrieval across data sets. For example, a number of patients that have received a specific treatment and are in remission may be determined (e.g., via a search).

Moreover, a system may extract specific FOV annotated images for inclusion into a structured output. Also, FOV images may be captured while maintaining annotated regions of interest as a metadata layer, and the FOV annotated images may be provided in a structured output into a CCD structure, which is compliant with the CDA. Furthermore, annotations and other information (e.g., information contained in an annotation, such as in a label and/or caption) may be stored with an image or inside of an image, and may be exported to, for example, the Consolidated-Clinical Document Architecture (C-CDA) standard for structured reporting. FOV images, including annotated regions of interest (e.g., visual, label, caption), may be collected for inclusion into the C-CDA structured output for consumption by an external system, and metadata (e.g., annotations) may include information, which may be processed by the external system. Further, a system may be configured to capture FOV images while maintaining annotated regions of interest (e.g., as a metadata layer) in a manner that is compliant with the Health Information Technology Standards Panel (HITSP) standard, which may allow for external consumption by a separate system.

In one embodiment, annotations (e.g., labels and captions) can be extended to contain discrete pieces of information for clinical documentation, billing and reimbursement, and can be used or reused by an external system to communicate with other external systems. Various embodiments may include tools for visually annotating images with, for example, symbols, labels, captions, billing codes, and vocabularies. These tools may allow for tracking events (e.g., during treatment planning), and, therefore, may allow information to be added as part of a documentation process. Documenting different and iterative cycles and maintaining a collection of information and knowledge generated by a care team becomes part of the encounter-based reporting and potentially billing. As an example, the addition of a semantic ontology may enable indexing and decision support, thereby extending the value of the information in the collection. Analytics companies can easily integrate with the system and use the collection of data for a variety of uses (e.g., clinical decision support, patient trending, and reimbursement trends).

Various embodiments, as disclosed herein, may be compliant with standard Health Level 7 (HL7) protocols for interfacing to external systems, Integrating the Healthcare Enterprise (IHE) profiles, as well as structured (XML, SVG) messaging for CCD transactions. Moreover, embodiments may be configured to adhere to standard security practices (e.g., maintain Health Insurance Portability and Accountability Act (HIPAA compliance) with user authentication in a role-based access control environment.

Figure 5:
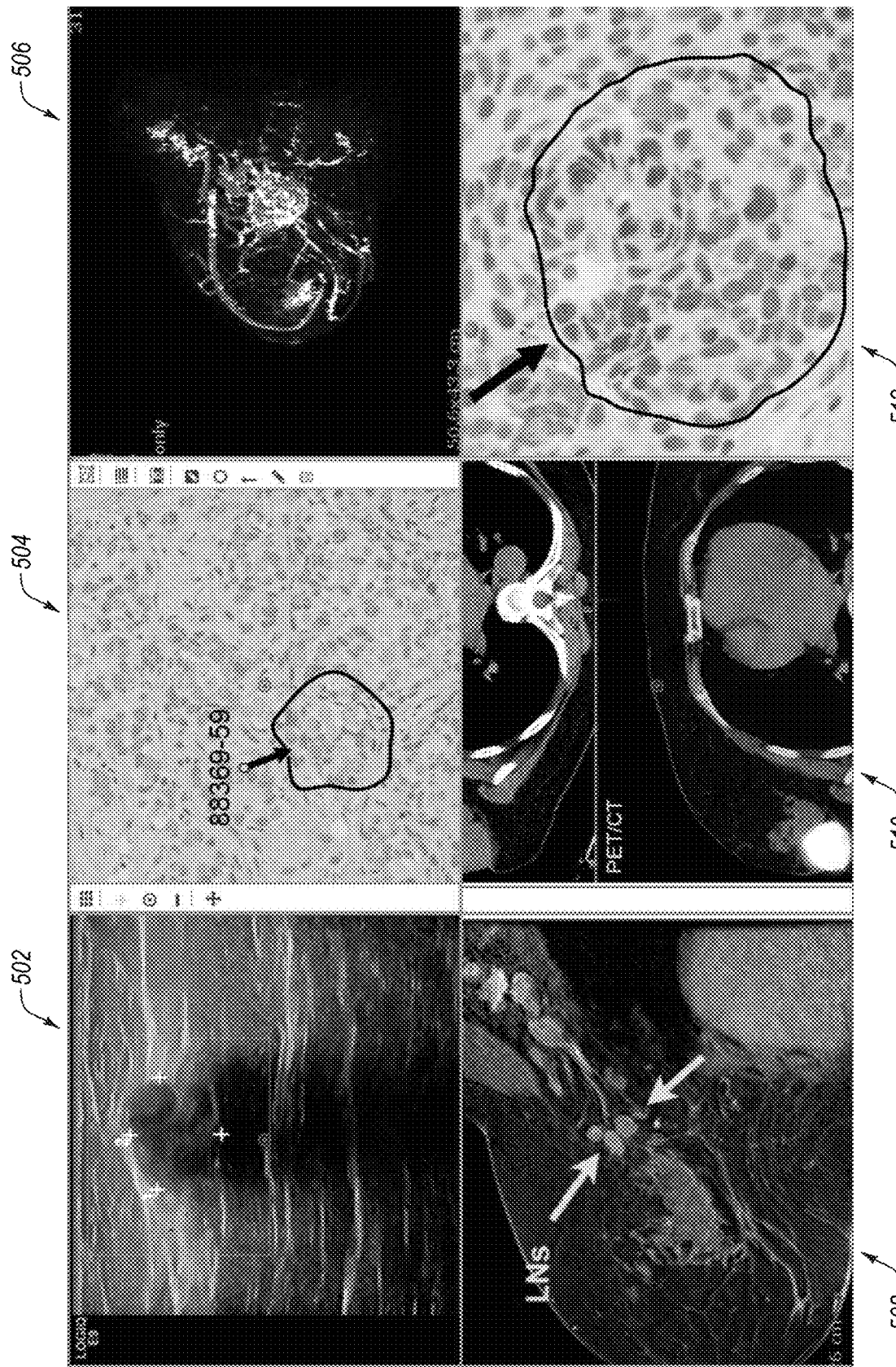
FIG. 5 is a screenshot including a plurality of images.

FIG. 5 is a screenshot including a plurality of images. More particularly, FIG. 5 is a screenshot (e.g., a presentation to a user interface) depicting a plurality of images, such as an ultrasound image 502, a progesterone receptor (PR) image 504, and a breast magnetic resonance imaging (MRI) image 506. FIG. 5 further includes a human epidermal growth factor receptor (HER2) image 512 depicting tissue biopsies presented together with breast MRI images 506 and 508. FIG. 8 further includes a positron emission tomography and computation tomography (PET/CT) 510, which may be used to determine the anatomic area and expression of genes that have an important role in the development and progression of certain aggressive types of breast cancer. As will be appreciated, FIG. 5 depicts annotations, such as lines, arrows, and codes, that may be maintained across at least some of the images, and may be used for, for example, document treatment planning, billing, and/or patient outcomes.

Figure 6:
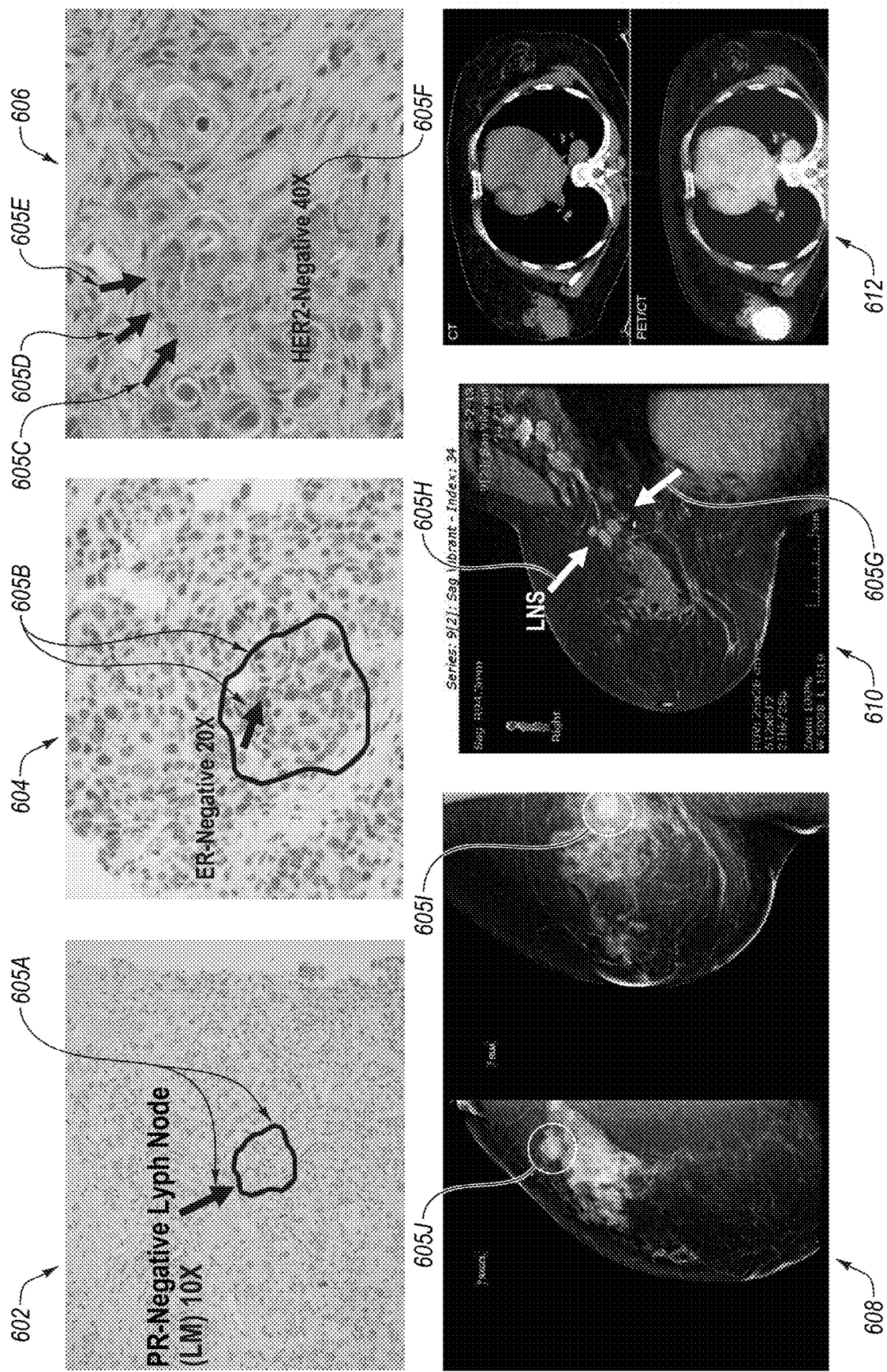
FIG. 6 depicts a plurality of images including annotations.

FIG. 6 depicts a plurality of images including annotations. More particularly, FIG. 6 depicts aggregated data including breast MRI 608 and 610, and colocalized PET/CT 612 linked to the tissue biopsies and stained ER 602, PR 604, and HER2 606. For example, one or more of the images depicted in FIG. 9 may be used in determining how much overexpressed HER2 protein is present and binding reactions or signals in a patient with triple negative breast carcinoma. The annotated regions of interest 605A and 605B (e.g., a line and an arrow) may link the specific regions of interest for each type of input and may provide the ability to compare, for example, the H&E and HER2 tissue biopsies. As will be appreciated, FIG. 6 depicts annotations 605 (e.g., lines, arrows, text, labels, circles and codes) that may be maintained across at least some of the images, and may be used for, for example, document treatment planning, billing, and/or patient outcomes.

Figure 7:
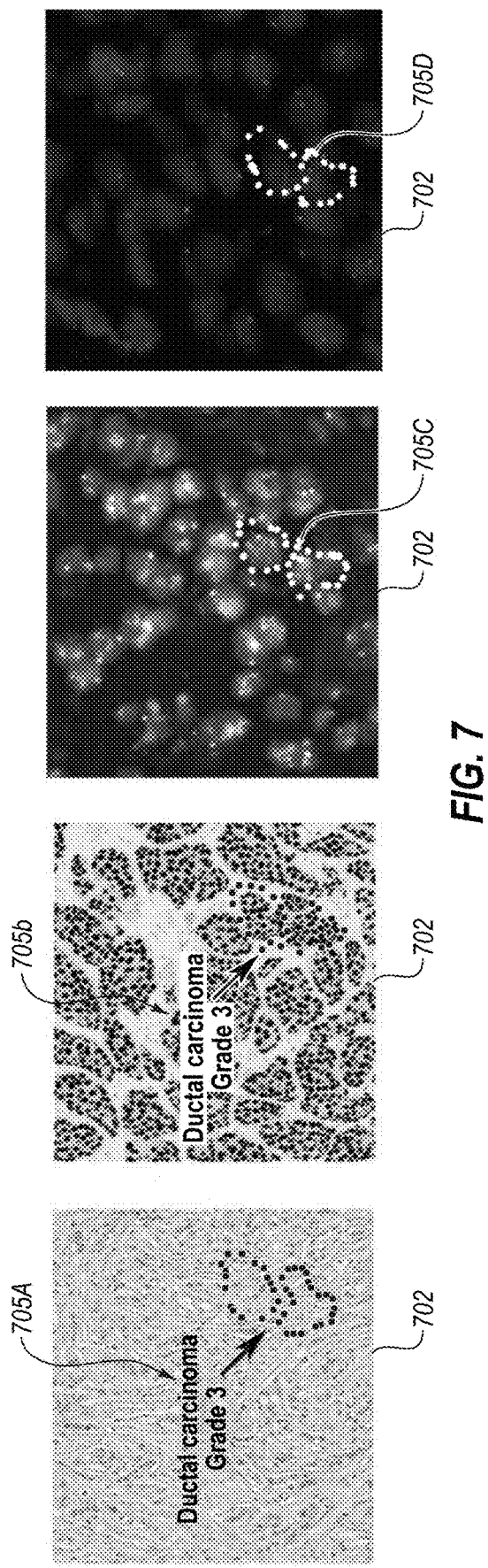
FIG. 7 depicts a plurality of images including annotations.

FIG. 7 depicts a plurality of images including annotations. More particularly, FIG. 7 depicts a plurality of images 702, 704, 706, and 708 from various modalities (i.e., H&E, Immunohistochemistry and FISH). FIG. 7 further depicts annotations 705A-705D. FIG. 7 illustrates an example of how cells identified in a FISH image may be mapped to H&E and HER2 images of stained tissue sample that have an established relationship for a variety of outputs. As will be appreciated, FIG. 7 depicts annotations 705 (e.g., lines, arrows, text, circles, labels, and codes) that may be maintained across at least some of the images, and may be used for, for example, document treatment planning, billing, and/or patient outcomes.

According to various embodiments, a system may enable an end-user to use annotation tools for drawing a region of interest (ROI) on various images, such as image 504 (see FIG. 5) with a Common Procedural Terminology (CPT) code (e.g., 88369), wherein the code may maintain a relationship in the system to a given image and cohort images. More specifically, codes may be used to link data (e.g., images) within a data set.

FIG. 8 depicts an example output. More particularly, FIG. 8 is an example output 800 which includes a CCD-A integrated report including annotated regions of interest. More specifically, FIG. 8 depicts an integrated report with annotated regions of interest for a breast cancer case. A CCD-A integrated report may be formatted such that it may render as a readable portable document or may be sent to a patient record in a structured format, which is consistent with the industry CCD-A communication standard. As illustrate, output 800 may include annotations.

Generating a report that encapsulates a collection of data (e.g., diagnostic events, specific FOV from images with annotated regions of interest (e.g., that document the expert findings across the multi-modality care continuum)) may be important for medical treatment (e.g., cancer treatment). According to various embodiments, FOV images may contain metadata that maintains relationships across a data set.

Some embodiments, as disclosed herein, relate generally to aggregating, organizing, and reporting in a standardized format and, more specifically, to collecting field of view images with metadata and aggregating that information with other patient information for generating one or more outputs (e.g., reports). It is understood that although FIGS. 5-8 generally disclose multiple medical images simultaneously rendered and displayed (with visual annotations) adjacent to one another in a single view, in some embodiments two or more medical images may additionally or alternatively be simultaneously rendered and displayed (with visual annotations) overlaying one another (e.g., on top of one another with a potentially adjustable level of transparency to allow for one or more images to be seen through the top image) to give additional context and for comparison purposes.

Figure 9:
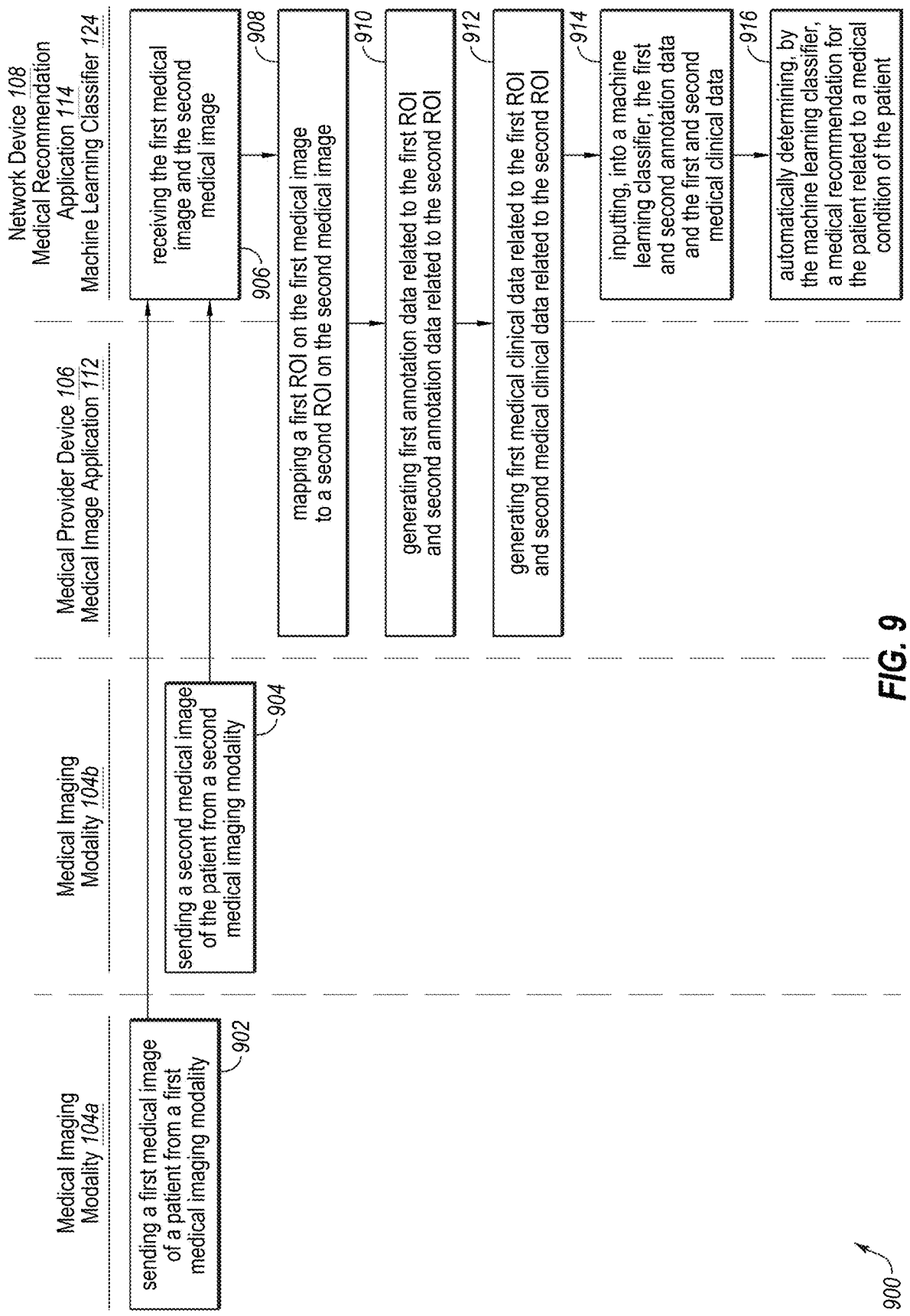
FIG. 9 is a flowchart of an example method for automatically determining a medical recommendation for a patient based on multiple medical images from multiple different medical imaging modalities.

FIG. 9 is a flowchart of an example method 900 for automatically determining a medical recommendation for a patient based on multiple medical images from multiple different medical imaging modalities. The method 900 may be performed, in some embodiments, by a device or system or application, such as by the medical imaging modalities 104a-104n, the medical provider device 106, the medical imaging application, the network device 108, and the medical recommendation application 114, or some combination thereof. In these and other embodiments, the method 900 may be performed by one or more processors based on one or more computer-readable instructions stored on one or more non-transitory computer-readable media. The method 900 will now be described in connection with FIGS. 1-9.

The method 900 may include, at action 902, sending a first medical image of a patient from a first medical imaging modality, at action 904, sending a second medical image of the patient from a second medical imaging modality, and at 906 receiving the first medical image and the second medical image. In some embodiments, the first medical imaging modality may be different from the second medical imaging modality. In some embodiments, the first medical imaging modality may include a computation tomography (CT) imaging modality, a magnetic resonance imaging (MRI) imaging modality, a histology pathology imaging modality, or a next generation sequenced (NGS) tissue/tumor microarray pathology imaging modality. In these embodiments, the second medical imaging modality may include a Fluorescence In Situ Hybridization (FISH) imaging modality, a flow cytometry pathology imaging modality, a gene or chromosomal microarray pathology imaging modality, or a myocardial perfusion radiology imaging modality. For example, the medical imaging modalities 104a and 104n may send, at actions 902 and 904, and the medical recommendation application 114 may receive, at action 906, the medical images 110a and 110n. In this example, both of the medical images 110a and 110n may be medical images generated from a single patient (e.g., the patient 103a), and may be generated from different types of imaging modalities, such as where the medical imaging modality 104a is an MM imaging modality and the medical imaging modality 104n in a TMA imaging modality.

The method 900 may include, at action 908, mapping a first ROI on the first medical image to a second ROI on the second medical image. In some embodiments, the first ROI and the second ROI may both be related to a medical condition of the patient. For example, a medical provider may employ the medical image application 112 to identify a first ROI on the medical image 110a and/or a second ROI on the medical image 110n related to a medical condition (e.g., breast cancer) of the patient 103a, and then the medical recommendation application 114 may automatically map, at action 908, the first ROI on the medical image 110a to the second ROI on the medical image 110n. In another example, the medical recommendation application 114 may automatically generate the first and/or second ROIs prior to mapping the first and second ROIs to one another. In another example, the second ROI may be generated based on the first ROI, such that the mapping of the first ROI to the second image results in the generation of the second ROI.

The method 900 may include, at action 910, generating first annotation data related to the first ROI and second annotation data related to the second ROI. For example, a medical provider may employ the medical image application 112 to generate, and/or the medical recommendation application 114 may automatically generate, at action 910, first annotation data related to the first ROI and second annotation data related to the second ROI (e.g., annotation data 120 related to the ROIs 118).

The method 900 may include, at action 912, generating first medical clinical data related to the first ROI and second medical clinical data related to the second ROI. In some embodiments, the first and second medical clinical data may include measurement data, blood flow data, opaqueness data, abnormality data, cellular structure data, or morphology data. For example, a medical provider may employ the medical image application 112 to generate, and/or the medical recommendation application 114 may automatically generate, at action 912, first medical clinical data related to the first ROI and second medical clinical data related to the second ROI (e.g., medical clinical data 122 related to the ROIs 118).

The method 900 may include, at action 914, inputting, into a machine learning classifier, the first and second annotation data and the first and second medical clinical data. For example, the medical recommendation application 114 may automatically input, at action 914, the first and second annotation data and the first and second medical clinical data (e.g., the annotation data 120 and the medical clinical data 122) into the machine learning classifier 124.

The method 900 may include, at action 916, automatically determining, by the machine learning classifier, a medical recommendation for the patient related to a medical condition of the patient. In some embodiments, the medical recommendation may include one or more of a diagnosis recommendation for the medical condition, a treatment recommendation for the medical condition, and a research recommendation for the medical condition. For example, the medical recommendation application 114 may employ the machine learning classifier 124 to automatically determine, at action 916, the medical recommendation 126 (e.g., a diagnosis recommendation, a treatment recommendation, or a research recommendation) for the patient 103a related to a medical condition (e.g., breast cancer) of the patient 103a.

In some embodiments, the method 900 may further include training the machine learning classifier. In some embodiments, this training may include training the machine learning classifier with annotation data and medical clinical data of medical images of one or more other patients. For example, the medical recommendation application 114 may gather the annotation data 120 and the medical clinical data 122 from patients other than the patient 103a, and also possibly from the patient 103a, and use the annotation data 120 and the medical clinical data 122 to train the machine learning classifier 124 to automatically generate medical recommendations. In this example, this training may occur periodically to continually improve the accuracy of the machine learning classifier 124.

In some embodiments, the method 900 may further include receiving a third medical image of the patient from the first medical imaging modality and a fourth medical image of the patient from the second medical imaging modality, mapping a third ROI on the third medical image to a fourth ROI on the fourth medical image with the third ROI and the fourth ROI both related to the medical condition of the patient, generating third annotation data related to the third ROI and fourth annotation data related to the fourth ROI, generating third medical clinical data related to the third ROI and fourth medical clinical data related to the fourth ROI, entering, into the machine learning classifier, the third and fourth annotation data and the third and fourth medical clinical data, and in response to the entering, automatically determining, by the machine learning classifier, an updated medical recommendation for the patient related to the medical condition of the patient. In these embodiments, the entering may further include reinputting, into the machine learning classifier, the first and second annotation data and the first and second medical clinical data. For example, the medical recommendation application 114 may receive one or more additional medical images of the patient 103a (in addition to the two medical images 110a and 110n), and may perform actions similar to actions 908-916 on these additional medical images in order to cause the machine learning classifier 124 to automatically determine an updated medical recommendation for the patient 103a related to the medical condition of the patient 103a. In this example, the third and fourth medical images may be updated versions of the first and second medical images (e.g., an updated Mill image and an updated TMA image), and then the machine learning classifier 124 may take the annotations and clinical data of the updated medical images and generate an updated recommendation for the patient's medical condition. Further, where the machine learning classifier 124 has also been trained with other patients' data in the meantime, the machine learning classifier 124 may be able to generate an even more accurate updated medical recommendation than when it generated the original medical recommendation. Also, where the entering of the third and fourth annotation data and medical clinical data in this example includes reinputting the first and second annotation data and medical clinical data and the first and second medical clinical data, the machine learning classifier 124 may consider annotation data and medical clinical data of the first pair of medical images along with same data from second (updated) pair of medical images in making its updated medical recommendation.

The method 900 may thus be employed, in some embodiments, to allow the medical recommendation application 114 to aggregate different medical images 116 of the patient 103a that were originally generated using the different medical imaging modalities 104a and 104n, as well as associated annotation data 120 and medical clinical data 122 related to a medical condition (e.g., breast cancer) of the patient 103a, and to allow the medical recommendation application 114 to automatically generate a medical recommendation 126 for the patient 103a related to the medical condition using the machine learning classifier 124.

Although the actions of the method 900 are illustrated in FIG. 9 as discrete actions, various actions may be divided into additional actions, combined into fewer actions, reordered, expanded, or eliminated, depending on the desired implementation. For example, in some embodiments, the method 900 may be performed without the action 902 and 904.

In some embodiments, where the structured annotations are key value pairs of information and are aggregated and stored in a database, each key value pair may contain a unique identifier and a value that contains identification and a pointer to a specific location identifying an ROI on a medical image from one modality. Also, each key value pair may contain metadata for area, perimeter, diameter, symmetry and/or volume of the ROI on one image from one modality and may map to the key value pair to an ROI on a medical image from a different modality. Further, each value-pair may be used to calculate specific characteristics that are mapped to a different image from a different image modality (e.g., clinical-diagnostic-clinical).

In some embodiments, clinical data may be associated with the structured annotations. For example, the structure of the annotations may contain descriptors that are related to the clinical data for each of the modalities of medical images. Further, the individual medical imaging modalities that contain clinical data may be related to clinical data from a system such as an EMR, LIS that is used in decision making.

In some embodiments, rules may be defined and applied to a collection of structured annotations, clinical data, and medical images from different medical imaging modalities. For example, a standardized data structure and data model may be applied to order the collection per patient and specific disease type (e.g., lung, breast, integument, colon, prostate, etc.). Also, standardized data structures may be extended to all aggregates based on patient and disease type to form one or more collections. Further one or more machine learning models (e.g., classifiers) may be trained based on a rule set of a standardized collection. Also, a trained machine learning model may be to predict future diagnostic events and patient outcomes based on the standardized data model.

In some embodiments, calculations from standardized rule sets to types of images of a same disease type (e.g., breast cancer) may be employed to identify statistically significant relationships to determine treatment pathways and outcomes. Further, calculations to derive standard determinations may be performed that can be applied to new image collections in a disease category (e.g., where a disease category is based on a disease type). Also, elements may be normalized and mapped into a common standard data model to compare an annotated image modality and a clinical data set to continuously increase a probability of effective diagnosis and treatment.

One example of structured annotation key value pairs may include a pathology image (histopathology) where properties contained in the visual annotation (e.g., a matrix of x, y, and z values related to the frame of reference or region of interest) contain a morphological region of interest described by medical/clinical input that is related to an image radiology image (clinical) that contains an ROI that is specific to radiology. In this example, the calculations performed to identify a specific ROI that contains anatomy that is defined by properties such as blood flow, abnormal anatomy, cellular structure, morphology (structural, physiological or spatial heterogeneity) across images from the modalities of radiology and pathology may be used to derive standard determinations that can be applied to new images to assist in diagnoses, treatment, and research.

Another example may include images related to breast cancer from radiology and pathology, each annotated with a structured annotation and one and two value pairs respectively, a value pair (e.g., a label) that contains a clinical description of findings (e.g., radiology) and diagnostic description (e.g., pathology) and a separate data input (e.g., a label) that identifies the lymph node derived from a radiology image being mapped to a micro dissected sample of tissue (e.g., pathology). The combination of the annotation and label inputs may identify affected anatomy pathology staining of cells from tissue and may organize the data inputs with the data set to predict a diagnosis.

Another example that continues with the breast cancer example of pathology imaging (e.g., histology) may include four images from the lymph node and stained with specific pathology stains to determine level, type and severity of breast cancer (e.g., ER/PR/HER2 negative). These may include annotations (e.g., arrows) and data inputs (e.g., lines and labels) of PR-Negative Lymph Node (LM) 10×; ER-Negative 20× and HER2 Negative 40× that have a specific relationship with a genetic result from tissue microarray to determine hereditary risk or determine if the patient and populations fall into the category for treatment (e.g., PARP inhibitor treatment). This example may be significant because PARP inhibitors may be very expensive drugs and guidelines that indicate whether a patient falls into a breast cancer treatment guideline (e.g., NCCN) are often outdated.

FIG. 10 illustrates an example computer system 1000 that may be employed in automatically determining a medical recommendation for a patient based on multiple medical images from multiple different medical imaging modalities. In some embodiments, the computer system 1000 may be part of any of the systems or devices described in this disclosure. For example, the computer system 1000 may be part of any of the medical imaging modalities 104a-104n, the medical provider device 106, and the network device 108 of FIG. 1.

The computer system 1000 may include a processor 1002, a memory 1004, a file system 1006, a communication unit 1008, an operating system 1010, a user interface 1012, and an application 1014, which all may be communicatively coupled. In some embodiments, the computer system may be, for example, a desktop computer, a client computer, a server computer, a mobile phone, a laptop computer, a smartphone, a smartwatch, a tablet computer, a portable music player, or any other computer system.

Generally, the processor 1002 may include any suitable special-purpose or general-purpose computer, computing entity, or processing device including various computer hardware or software applications and may be configured to execute instructions stored on any applicable computer-readable storage media. For example, the processor 1002 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data, or any combination thereof. In some embodiments, the processor 1002 may interpret and/or execute program instructions and/or process data stored in the memory 1004 and/or the file system 1006. In some embodiments, the processor 1002 may fetch program instructions from the file system 1006 and load the program instructions into the memory 1004. After the program instructions are loaded into the memory 1004, the processor 1002 may execute the program instructions. In some embodiments, the instructions may include the processor 1002 performing one or more actions of the method 900 of FIG. 9.

The memory 1004 and the file system 1006 may include computer-readable storage media for carrying or having stored thereon computer-executable instructions or data structures. Such computer-readable storage media may be any available non-transitory media that may be accessed by a general-purpose or special-purpose computer, such as the processor 1002. By way of example, and not limitation, such computer-readable storage media may include non-transitory computer-readable storage media including Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage media which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 1002 to perform a certain operation or group of operations, such as one or more actions of the method 900 of FIG. 9. These computer-executable instructions may be included, for example, in the operating system 1010, in one or more applications, such as the medical image application 112 or the medical recommendation application 114 of FIG. 1, or in some combination thereof.

The communication unit 1008 may include any component, device, system, or combination thereof configured to transmit or receive information over a network, such as the network 102 of FIG. 1. In some embodiments, the communication unit 1008 may communicate with other devices at other locations, the same location, or even other components within the same system. For example, the communication unit 1008 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, a cellular communication device, etc.), and/or the like. The communication unit 1008 may permit data to be exchanged with a network and/or any other devices or systems, such as those described in the present disclosure.

The operating system 1010 may be configured to manage hardware and software resources of the computer system 1000 and configured to provide common services for the computer system 1000.

The user interface 1012 may include any device configured to allow a user to interface with the computer system 1000. For example, the user interface 1012 may include a display, such as an LCD, LED, or other display, that is configured to present video, text, application user interfaces, and other data as directed by the processor 1002. The user interface 1012 may further include a mouse, a track pad, a keyboard, a touchscreen, volume controls, other buttons, a speaker, a microphone, a camera, any peripheral device, or other input or output device. The user interface 1012 may receive input from a user and provide the input to the processor 1002. Similarly, the user interface 1012 may present output to a user.

The application 1014 may be one or more computer-readable instructions stored on one or more non-transitory computer-readable media, such as the memory 1004 or the file system 1006, that, when executed by the processor 1002, is configured to perform one or more actions of the method 900 of FIG. 9. In some embodiments, the application 1014 (e.g., app) may be part of the operating system 1010 or may be part of an application of the computer system 1000, or may be some combination thereof. In some embodiments, the application 1014 may function as any of the medical image application 112 or the medical recommendation application 114 of FIG. 1.

Modifications, additions, or omissions may be made to the computer system 1000 without departing from the scope of the present disclosure. For example, although each is illustrated as a single component in FIG. 10, any of the components 1002-1014 of the computer system 1000 may include multiple similar components that function collectively and are communicatively coupled. Further, although illustrated as a single computer system, it is understood that the computer system 1000 may include multiple physical or virtual computer systems that are networked together, such as in a cloud computing environment, a multitenancy environment, or a virtualization environment.

As indicated above, the embodiments described herein may include the use of a special purpose or general-purpose computer (e.g., the processor 1002 of FIG. 10) including various computer hardware or software applications, as discussed in greater detail below. Further, as indicated above, embodiments described herein may be implemented using computer-readable media (e.g., the memory 1004 or file system 1006 of FIG. 10) for carrying or having computer-executable instructions or data structures stored thereon.

In some embodiments, the different components and applications described herein may be implemented as objects or processes that execute on a computer system (e.g., as separate threads). While some of the methods described herein are generally described as being implemented in software (stored on and/or executed by general purpose hardware), specific hardware implementations or a combination of software and specific hardware implementations are also possible and contemplated.

In accordance with common practice, the various features illustrated in the drawings may not be drawn to scale. The illustrations presented in the present disclosure are not meant to be actual views of any particular apparatus (e.g., device, system, etc.) or method, but are merely example representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the summary, detailed description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The foregoing description, for purpose of explanation, has been described with reference to specific embodiments. However, the illustrative discussions above are not intended to be exhaustive or to limit the invention as claimed to the precise forms disclosed. Many modifications and variations are possible in view of the above teachings. The embodiments were chosen and described to explain practical applications, to thereby enable others skilled in the art to utilize the invention as claimed and various embodiments with various modifications as may be suited to the particular use contemplated.

What is claimed is:

1. A computer-implemented method for automatically determining a medical recommendation for a patient based on multiple medical images from multiple different medical imaging modalities, the computer-implemented method comprising:
   receiving a first medical image of a patient from a first medical imaging modality and a second medical image of the patient from a second medical imaging modality, the first medical imaging modality being different from the second medical imaging modality;

mapping a first region of interest (ROI) on the first medical image to a second ROI on the second medical image, the first ROI and the second ROI both related to a medical condition of the patient, wherein each of the first ROI and the second ROI includes a feature contained in the corresponding medical image, the feature selected from a list that includes nodule(s), morphology, gross anatomy, structure, color, and shape;

generating first annotation data related to the first ROI and second annotation data related to the second ROI;

generating first medical clinical data related to the first ROI and second medical clinical data related to the second ROI;

training a machine learning classifier with annotation data and medical clinical data of medical images of one or more other patients;

inputting, into the machine learning classifier, the first and second annotation data and the first and second medical clinical data; and in response to the inputting, automatically determining, by the machine learning classifier, a medical recommendation for the patient related to the medical condition of the patient.

2. The computer-implemented method of claim 1, further comprising: receiving a third medical image of the patient from the first medical imaging modality and a fourth medical image of the patient from the second medical imaging modality; mapping a third ROI on the third medical image to a fourth ROI on the fourth medical image, the third ROI and the fourth ROI both related to the medical condition of the patient; generating third annotation data related to the third ROI and fourth annotation data related to the fourth ROI; generating third medical clinical data related to the third ROI and fourth medical clinical data related to the fourth ROI; entering, into the machine learning classifier, the third and fourth annotation data and the third and fourth medical clinical data; and in response to the entering, automatically determining, by the machine learning classifier, an updated medical recommendation for the patient related to the medical condition of the patient.

3. The computer-implemented method of claim 2, wherein the entering further comprises reinputting, into the machine learning classifier, the first and second annotation data and the first and second medical clinical data.

4. The computer-implemented method of claim 1, wherein the medical recommendation includes one or more of a diagnosis recommendation for the medical condition, a treatment recommendation for the medical condition, and a research recommendation for the medical condition.

5. The computer-implemented method of claim 1, wherein:
the first medical imaging modality comprises a computation tomography (CT) imaging modality, a magnetic resonance imaging (MRI) imaging modality, a histology pathology imaging modality, or a next generation sequenced (NGS) tissue/tumor microarray pathology imaging modality; and
the second medical imaging modality comprises a tissue microarray (TMA) imaging modality, a Fluorescence In Situ Hybridization (FISH) imaging modality, a flow cytometry pathology imaging modality, a gene or chromosomal microarray pathology imaging modality, or a myocardial perfusion radiology imaging modality.

6. The computer-implemented method of claim 1, wherein the first and second medical clinical data comprise measurement data, blood flow data, opaqueness data, abnormality data, cellular structure data, or morphology data.

7. One or more non-transitory computer-readable media comprising one or more computer readable instructions that, when executed by one or more processors of a computing device, cause the computing device to perform a method for automatically determining a medical recommendation for a patient based on multiple medical images from multiple different medical imaging modalities, the method comprising:

receiving a first medical image of a patient from a first medical imaging modality and a second medical image of the patient from a second medical imaging modality, the first medical imaging modality being different from the second medical imaging modality;

mapping a first region of interest (ROI) on the first medical image to a second ROI on the second medical image, the first ROI and the second ROI both related to a medical condition of the patient;

generating first annotation data related to the first ROI and second annotation data related to the second ROI;

generating first medical clinical data related to the first ROI and second medical clinical data related to the second ROI;

training a machine learning classifier with annotation data and medical clinical data of medical images of one or more other patients, including;
applying a standardized data structure and data model to a collection of structured annotations, clinical data, and medical images from different medical imaging modalities and for the one or more other patients to order the collection per patient and specific disease type;
extending standardized data structures to all aggregates based on patient and disease type to form one or more standardized collections; and
training the machine learning classifier based on one or more rule sets of the one or more standardized collections;

inputting, into the machine learning classifier, the first and second annotation data and the first and second medical clinical data; and in response to the inputting, automatically determining, by the machine learning classifier, a medical recommendation for the patient related to the medical condition of the patient.

8. The one or more non-transitory computer-readable media of claim 7, wherein the method further comprises: receiving a third medical image of the patient from the first medical imaging modality and a fourth medical image of the patient from the second medical imaging modality; mapping a third ROI on the third medical image to a fourth ROI on the fourth medical image, the third ROI and the fourth ROI both related to the medical condition of the patient; generating third annotation data related to the third ROI and fourth annotation data related to the fourth ROI; generating third medical clinical data related to the third ROI and fourth medical clinical data related to the fourth ROI; entering, into the machine learning classifier, the third and fourth annotation data and the third and fourth medical clinical data; and in response to the entering, automatically determining, by the machine learning classifier, an updated medical recommendation for the patient related to the medical condition of the patient.

9. The one or more non-transitory computer-readable media of claim 8, wherein the entering further comprises reinputting, into the machine learning classifier, the first and second annotation data and the first and second medical clinical data.

10. The one or more non-transitory computer-readable media of claim 7, wherein the medical recommendation includes one or more of a diagnosis recommendation for the medical condition, a treatment recommendation for the medical condition, and a research recommendation for the medical condition.

11. The one or more non-transitory computer-readable media of claim 7, wherein:
the first medical imaging modality comprises a computation tomography (CT) imaging modality, a magnetic resonance imaging (MRI) imaging modality, a histology pathology imaging modality, or a next generation sequenced (NGS) tissue/tumor microarray pathology imaging modality; and
the second medical imaging modality comprises a tissue microarray (TMA) imaging modality, a Fluorescence In Situ Hybridization (FISH) imaging modality, a flow cytometry pathology imaging modality, a gene or chromosomal microarray pathology imaging modality, or a myocardial perfusion radiology imaging modality.

12. The one or more non-transitory computer-readable media of claim 7, wherein the first and second medical clinical data comprise measurement data, blood flow data, opaqueness data, abnormality data, cellular structure data, or morphology data.

13. A computing device comprising:
one or more processors; and
one or more non-transitory computer-readable media comprising one or more computer readable instructions that, when executed by the one or more processors, cause the computing device to perform a method for automatically determining a medical recommendation for a patient based on multiple medical images from multiple different medical imaging modalities, the method comprising:
receiving a first medical image of a patient from a first medical imaging modality and a second medical image of the patient from a second medical imaging modality, the first medical imaging modality being different from the second medical imaging modality;
mapping a first region of interest (ROI) on the first medical image to a second ROI on the second medical image, the first ROI and the second ROI both related to a medical condition of the patient;
generating first annotation data related to the first ROI and second annotation data related to the second ROI;
generating first medical clinical data related to the first ROI and second medical clinical data related to the second ROI;
training a machine learning classifier with annotation data and medical clinical data of medical images of one or more other patients;
inputting, into a machine learning classifier, the first and second annotation data and the first and second medical clinical data; and
in response to the inputting, automatically determining, by the machine learning classifier, a medical recommendation for the patient related to the medical condition of the patient and predicting one or more future diagnostic events or one or more patient outcomes of the patient.

14. The computing device of claim 13, wherein the method further comprises: receiving a third medical image of the patient from the first medical imaging modality and a fourth medical image of the patient from the second medical imaging modality; mapping a third ROI on the third medical image to a fourth ROI on the fourth medical image, the third ROI and the fourth ROI both related to the medical condition of the patient; generating third annotation data related to the third ROI and fourth annotation data related to the fourth ROI; generating third medical clinical data related to the third ROI and fourth medical clinical data related to the fourth ROI; entering, into the machine learning classifier, the third and fourth annotation data and the third and fourth medical clinical data; and in response to the entering, automatically determining, by the machine learning classifier, an updated medical recommendation for the patient related to the medical condition of the patient.

15. The computing device of claim 13, wherein the medical recommendation includes one or more of a diagnosis recommendation for the medical condition, a treatment recommendation for the medical condition, and a research recommendation for the medical condition.

16. The computing device of claim 13, wherein:
the first medical imaging modality comprises a computation tomography (CT) imaging modality, a magnetic resonance imaging (MRI) imaging modality, a histology pathology imaging modality, or a next generation sequenced (NGS) tissue/tumor microarray pathology imaging modality; and
the second medical imaging modality comprises a tissue microarray (TMA) imaging modality, a Fluorescence In Situ Hybridization (FISH) imaging modality, a flow cytometry pathology imaging modality, a gene or chromosomal microarray pathology imaging modality, or a myocardial perfusion radiology imaging modality.

17. The computing device of claim 13, wherein the first and second medical clinical data comprise measurement data, blood flow data, opaqueness data, abnormality data, cellular structure data, or morphology data.

18. One or more non-transitory computer-readable media comprising one or more computer readable instructions that, when executed by one or more processors of a computing device, cause the computing device to perform a method for automatically determining a medical recommendation for a patient based on multiple medical images from multiple different medical imaging modalities, the method comprising:
receiving a first medical image of a patient from a first medical imaging modality and a second medical image of the patient from a second medical imaging modality, the first medical imaging modality being different from the second medical imaging modality;
mapping a first region of interest (ROI) on the first medical image to a second ROI on the second medical image, the first ROI and the second ROI both related to a medical condition of the patient, wherein each of the first ROI and the second ROI includes a feature contained in the corresponding medical image, the feature selected from a list that includes nodule(s), morphology, gross anatomy, structure, color, and shape;
generating first annotation data related to the first ROI and second annotation data related to the second ROI;
generating first medical clinical data related to the first ROI and second medical clinical data related to the second ROI;
training a machine learning classifier with annotation data and medical clinical data of medical images of one or more other patients;
inputting, into the machine learning classifier, the first and second annotation data and the first and second medical clinical data; and in response to the inputting, automatically determining, by the machine learning classifier, a medical recommendation for the patient related to the medical condition of the patient.

19. A computing device comprising:
one or more processors; and
one or more non-transitory computer-readable media comprising one or more computer readable instructions that, when executed by the one or more processors, cause the computing device to perform a method for automatically determining a medical recommendation for a patient based on multiple medical images from multiple different medical imaging modalities, the method comprising:
receiving a first medical image of a patient from a first medical imaging modality and a second medical image of the patient from a second medical imaging modality, the first medical imaging modality being different from the second medical imaging modality;
mapping a first region of interest (ROI) on the first medical image to a second ROI on the second medical image, the first ROI and the second ROI both related to a medical condition of the patient, wherein each of the first ROI and the second ROI includes a feature contained in the corresponding medical image, the feature selected from a list that includes nodule(s), morphology, gross anatomy, structure, color, and shape;
generating first annotation data related to the first ROI and second annotation data related to the second ROI;
generating first medical clinical data related to the first ROI and second medical clinical data related to the second ROI;
training a machine learning classifier with annotation data and medical clinical data of medical images of one or more other patients;
inputting, into the machine learning classifier, the first and second annotation data and the first and second medical clinical data; and
in response to the inputting, automatically determining, by the machine learning classifier, a medical recommendation for the patient related to the medical condition of the patient.

20. A computer-implemented method for automatically determining a medical recommendation for a patient based on multiple medical images from multiple different medical imaging modalities, the computer-implemented method comprising:
receiving a first medical image of a patient from a first medical imaging modality and a second medical image of the patient from a second medical imaging modality, the first medical imaging modality being different from the second medical imaging modality;
mapping a first region of interest (ROI) on the first medical image to a second ROI on the second medical image, the first ROI and the second ROI both related to a medical condition of the patient;
generating first annotation data related to the first ROI and second annotation data related to the second ROI;
generating first medical clinical data related to the first ROI and second medical clinical data related to the second ROI;
training a machine learning classifier with annotation data and medical clinical data of medical images of one or more other patients, including:
applying a standardized data structure and data model to a collection of structured annotations, clinical data, and medical images from different medical imaging modalities and for the one or more other patients to order the collection per patient and specific disease type;
extending standardized data structures to all aggregates based on patient and disease type to form one or more standardized collections; and
training the machine learning classifier based on one or more rule sets of the one or more standardized collections;
inputting, into the machine learning classifier, the first and second annotation data and the first and second medical clinical data; and
in response to the inputting, automatically determining, by the machine learning classifier, a medical recommendation for the patient related to the medical condition of the patient.

21. A computing device comprising:
one or more processors; and
one or more non-transitory computer-readable media comprising one or more computer readable instructions that, when executed by the one or more processors, cause the computing device to perform a method for automatically determining a medical recommendation for a patient based on multiple medical images from multiple different medical imaging modalities, the method comprising:
receiving a first medical image of a patient from a first medical imaging modality and a second medical image of the patient from a second medical imaging modality, the first medical imaging modality being different from the second medical imaging modality;
mapping a first region of interest (ROI) on the first medical image to a second ROI on the second medical image, the first ROI and the second ROI both related to a medical condition of the patient;
generating first annotation data related to the first ROI and second annotation data related to the second ROI;
generating first medical clinical data related to the first ROI and second medical clinical data related to the second ROI;
training a machine learning classifier with annotation data and medical clinical data of medical images of one or more other patients, including:
applying a standardized data structure and data model to a collection of structured annotations, clinical data, and medical images from different medical imaging modalities and for the one or more other patients to order the collection per patient and specific disease type;
extending standardized data structures to all aggregates based on patient and disease type to form one or more standardized collections; and
training the machine learning classifier based on one or more rule sets of the one or more standardized collections;
inputting, into the machine learning classifier, the first and second annotation data and the first and second medical clinical data; and
in response to the inputting, automatically determining, by the machine learning classifier, a medical recommendation for the patient related to the medical condition of the patient.

22. A computer-implemented method for automatically determining a medical recommendation for a patient based on multiple medical images from multiple different medical imaging modalities, the computer-implemented method comprising:

receiving a first medical image of a patient from a first medical imaging modality and a second medical image of the patient from a second medical imaging modality, the first medical imaging modality being different from the second medical imaging modality;

mapping a first region of interest (ROI) on the first medical image to a second ROI on the second medical image, the first ROI and the second ROI both related to a medical condition of the patient;

generating first annotation data related to the first ROI and second annotation data related to the second ROI;

generating first medical clinical data related to the first ROI and second medical clinical data related to the second ROI;

training a machine learning classifier with annotation data and medical clinical data of medical images of one or more other patients;

inputting, into a machine learning classifier, the first and second annotation data and the first and second medical clinical data; and in response to the inputting, automatically determining, by the machine learning classifier, a medical recommendation for the patient related to the medical condition of the patient and predicting one or more future diagnostic events or one or more patient outcomes of the patient.

23. One or more non-transitory computer-readable media comprising one or more computer readable instructions that, when executed by one or more processors of a computing device, cause the computing device to perform a method for automatically determining a medical recommendation for a patient based on multiple medical images from multiple different medical imaging modalities, the method comprising:

receiving a first medical image of a patient from a first medical imaging modality and a second medical image of the patient from a second medical imaging modality, the first medical imaging modality being different from the second medical imaging modality;

mapping a first region of interest (ROI) on the first medical image to a second ROI on the second medical image, the first ROI and the second ROI both related to a medical condition of the patient;

generating first annotation data related to the first ROI and second annotation data related to the second ROI;

generating first medical clinical data related to the first ROI and second medical clinical data related to the second ROI;

training a machine learning classifier with annotation data and medical clinical data of medical images of one or more other patients;

inputting, into a machine learning classifier, the first and second annotation data and the first and second medical clinical data; and in response to the inputting, automatically determining, by the machine learning classifier, a medical recommendation for the patient related to the medical condition of the patient and predicting one or more future diagnostic events or one or more patient outcomes of the patient.

\* \* \* \* \*